US009345741B2

(12) United States Patent
Hondmann et al.

(10) Patent No.: US 9,345,741 B2
(45) Date of Patent: May 24, 2016

(54) NUTRITIONAL COMPOSITION CONTAINING A PEPTIDE COMPONENT WITH ADIPONECTIN SIMULATING PROPERTIES AND USES THEREOF

(71) Applicant: Mead Johnson Nutrition Company, Glenview, IL (US)

(72) Inventors: Dirk Hondmann, Winnetka, IL (US); Eric A. F. Van Tol, Arnhem (NL); Gabriele Gross, Nijmegen (NL); Marieke H. Schoemaker, Rhenen (NL); Teartse Tim Lambers, Nijmegen (NL); Tania Ramacho, Dusseldorf (DE); Manuela Elsen, Dusseldorf (DE); Jürgen Eckel, Dusseldorf (DE)

(73) Assignee: Mead Johnson Nutrition Company, Glenview, IL (US)

( * ) Notice: Subject to any disclaimer, the term of this patent is extended or adjusted under 35 U.S.C. 154(b) by 0 days.

(21) Appl. No.: 13/833,039

(22) Filed: Mar. 15, 2013

(65) Prior Publication Data
US 2014/0271586 A1 Sep. 18, 2014

(51) Int. Cl.
| A01N 63/00 | (2006.01) |
| A61K 35/20 | (2006.01) |
| A61K 38/08 | (2006.01) |
| A23L 1/30 | (2006.01) |
| A23L 1/305 | (2006.01) |
| A61K 35/745 | (2015.01) |
| A61K 35/747 | (2015.01) |
| A61K 38/07 | (2006.01) |
| A23J 3/34 | (2006.01) |
| A61K 38/01 | (2006.01) |
| A23L 1/29 | (2006.01) |

(52) U.S. Cl.
CPC ............... *A61K 38/08* (2013.01); *A23J 3/344* (2013.01); *A23L 1/296* (2013.01); *A23L 1/3008* (2013.01); *A23L 1/3014* (2013.01); *A23L 1/3053* (2013.01); *A61K 35/745* (2013.01); *A61K 35/747* (2013.01); *A61K 38/018* (2013.01); *A61K 38/07* (2013.01); *A23V 2002/00* (2013.01)

(58) Field of Classification Search
CPC ............................... A01N 63/00; A61K 35/20
See application file for complete search history.

(56) References Cited

U.S. PATENT DOCUMENTS

| 3,876,766 A | 4/1975 | Frommer et al. |
| 3,937,817 A | 2/1976 | Frommer et al. |
| 4,016,260 A | 4/1977 | Karasaki et al. |
| 4,358,465 A | 11/1982 | Brule et al. |
| 4,361,587 A | 11/1982 | Brule et al. |
| 4,491,589 A | 1/1985 | Dell et al. |
| 4,902,501 A | 2/1990 | Bandi et al. |
| 5,102,871 A | 4/1992 | Furukawa et al. |
| 5,112,812 A | 5/1992 | Samuelsson et al. |
| 5,230,902 A | 7/1993 | Gold et al. |
| 5,308,832 A | 5/1994 | Garleb et al. |
| 5,405,637 A | 4/1995 | Martinez et al. |
| 5,605,893 A | 2/1997 | Kaufman |
| 5,643,880 A | 7/1997 | Mukerji et al. |
| 5,714,472 A | 2/1998 | Gray et al. |
| 5,723,446 A | 3/1998 | Gray et al. |
| 5,821,217 A | 10/1998 | Forse et al. |
| 6,077,558 A | 6/2000 | Euber |
| 6,451,368 B1 | 9/2002 | Elliott et al. |
| 6,451,552 B1 | 9/2002 | van Beresteijn et al. |
| 6,468,962 B1 | 10/2002 | Portman |
| 6,713,082 B2 | 3/2004 | van Loon et al. |
| 6,875,456 B2 | 4/2005 | Delest et al. |
| 6,905,702 B1 | 6/2005 | Kaufman |
| 7,022,676 B2 | 4/2006 | Tamura et al. |
| 7,214,521 B2 | 5/2007 | Wada et al. |
| 7,258,996 B2 | 8/2007 | Jullerat et al. |
| 7,501,490 B2 | 3/2009 | Kadowaki et al. |
| 7,563,458 B2 | 7/2009 | Kume et al. |
| 7,648,721 B2 | 1/2010 | Edens et al. |
| 7,648,957 B2 | 1/2010 | Heyden et al. |
| 7,666,996 B2 | 2/2010 | Sidelman |
| 7,741,274 B2 | 6/2010 | Sidelman |
| 7,785,824 B2 | 8/2010 | van der Burg-Koorevaar et al. |

(Continued)

FOREIGN PATENT DOCUMENTS

| CA | 2340223 | 2/2000 |
| DE | 102004040452 | 2/2006 |

(Continued)

OTHER PUBLICATIONS

Swanson Best Weight-Control Formulas. Maximum-Stength Adiponectin Activation Formula. 2013.*

(Continued)

*Primary Examiner* — Karen Cochrane Carlson
*Assistant Examiner* — Natalie Moss
(74) *Attorney, Agent, or Firm* — Patterson Intellectual Property Law, P.C; James R. Cartiglia; Bethany J. Whelan

(57) ABSTRACT

The present disclosure relates to nutritional compositions including a protein equivalent source that includes a peptide component comprising selected peptides. The protein equivalent source may further include intact protein, hydrolyzed protein, including partially hydrolyzed protein, or combinations thereof. The disclosure further relates to methods of promoting healthy body weight in a target subject by stimulating adiponectin levels by providing the nutritional compositions disclosed herein to a target subject, which includes a pediatric subject.

18 Claims, 1 Drawing Sheet

(56) References Cited

U.S. PATENT DOCUMENTS

| | | | |
|---|---|---|---|
| 7,972,808 | B2 | 7/2011 | Edens et al. |
| 8,119,142 | B2 | 2/2012 | Zwijsen et al. |
| 8,129,337 | B2 | 3/2012 | Wolfram |
| 8,273,710 | B2 | 9/2012 | Boots |
| 8,343,531 | B2 | 1/2013 | Morifuji et al. |
| 8,354,502 | B2 | 1/2013 | Recio Sanchez et al. |
| 8,367,614 | B2 | 2/2013 | Hatori et al. |
| 2002/0147144 | A1 | 10/2002 | Sidelman |
| 2003/0138476 | A1 | 7/2003 | van Leeuwen et al. |
| 2004/0063633 | A1 | 4/2004 | Hayasawa et al. |
| 2005/0019372 | A1 | 1/2005 | Corkey et al. |
| 2005/0089969 | A1 | 4/2005 | Wissler et al. |
| 2004/0510088 | | 7/2005 | Katunuma et al. |
| 2006/0234942 | A1 | 10/2006 | Tauzin et al. |
| 2006/0286208 | A1* | 12/2006 | Rangavajla ............... A63J 3/34 426/34 |
| 2007/0031399 | A1 | 2/2007 | Edens et al. |
| 2007/0060519 | A1 | 3/2007 | Rozing et al. |
| 2004/0576834 | | 5/2007 | Stahl et al. |
| 2007/0203060 | A1 | 8/2007 | Sidelman |
| 2008/0031814 | A1 | 2/2008 | Hageman |
| 2008/0075828 | A1 | 3/2008 | Wolfram et al. |
| 2008/0096794 | A1 | 4/2008 | Boehm et al. |
| 2008/0108548 | A1 | 5/2008 | Luyer et al. |
| 2006/0587324 | | 6/2008 | Geerlings et al. |
| 2004/0586563 | | 9/2008 | Huybrechts |
| 2008/0221023 | A1 | 9/2008 | Boots |
| 2009/0036351 | A1 | 2/2009 | Boots |
| 2009/0074893 | A1 | 3/2009 | de Waard et al. |
| 2009/0075904 | A1 | 3/2009 | Boots |
| 2009/0123605 | A1 | 5/2009 | van Benthum et al. |
| 2009/0131331 | A1 | 5/2009 | Edens et al. |
| 2009/0203592 | A1 | 8/2009 | Beerman et al. |
| 2009/0252729 | A1 | 10/2009 | Farrington et al. |
| 2009/0305945 | A1 | 12/2009 | Wolfram et al. |
| 2009/0318366 | A1 | 12/2009 | Edens et al. |
| 2009/0325888 | A1 | 12/2009 | Edens et al. |
| 2010/0047393 | A1 | 2/2010 | Glas et al. |
| 2010/0099607 | A1 | 4/2010 | Chen |
| 2010/0143262 | A1 | 6/2010 | Valenta et al. |
| 2010/0256235 | A1 | 10/2010 | Puder et al. |
| 2010/0306864 | A1 | 12/2010 | Tsuji et al. |
| 2011/0177044 | A1* | 7/2011 | Thomas ............... A23L 1/293 424/93.45 |
| 2011/0195153 | A1 | 8/2011 | Valenta et al. |
| 2012/0071400 | A1 | 3/2012 | Serizawa et al. |
| 2012/0142588 | A1 | 6/2012 | Rozing et al. |
| 2012/0322726 | A1 | 12/2012 | Somoto et al. |

FOREIGN PATENT DOCUMENTS

| | | |
|---|---|---|
| EP | 0274939 | 7/1988 |
| EP | 0448511 | 9/1991 |
| EP | 0629350 | 12/1994 |
| EP | 0418593 | 3/1997 |
| EP | 0791357 | 8/1997 |
| EP | 2017283 | 1/2009 |
| EP | 2332428 | 6/2011 |
| WO | 9111918 | 8/1991 |
| WO | 9212711 | 8/1992 |
| WO | 9802165 | 1/1998 |
| WO | 0137850 | 5/2001 |
| WO | 2005081628 | 9/2005 |
| WO | 2005117933 | 12/2005 |
| WO | 2006068480 | 6/2006 |
| WO | 2007064208 | 6/2007 |
| WO | 2008004794 | 1/2008 |
| WO | 2008054192 | 5/2008 |
| WO | 2008056983 | 5/2008 |
| WO | 2008108651 | 9/2008 |
| WO | 2009033737 | 3/2009 |
| WO | 2010043724 | 4/2010 |
| WO | 2011031149 | 3/2011 |
| WO | 2011069042 | 6/2011 |
| WO | 2012143362 | 10/2012 |

OTHER PUBLICATIONS

Ebner et al., "Nonallergic individuals recognize the same T cell epitopes of Bet v 1, the major birch pollen allergen, as atopic patients," J. Immunol. 1995, vol. 154, pp. 1932-1940.

Elsayed et al., "T cell recognition pattern of bovine milk αS1-casein and its peptides," Mol. Immunol. 2004, vol. 41 (12), pp. 1225-1234.

Hirahara et al., K., Profound immunological tolerance in the antibody response against bovine alpha s1-casein induced by intradermal administration of a dominant T cell determinant,: Clinical Immunology and Immunophathology, vol. 76, No. 1, 1995, pp. 12-18.

Knip, M., et al., "Dietary Intervention in Infancy and Later Signs of Beta-Cell Autoimmunity," N Engl J Med 2010;363:1900-8.

Kondo et al., "The Response of bovine beta-lactoglobulin-specific T-cell clones to single amino acid substitution of T-cell core epitope," Pediatr. Allergy Immunol. 2008, vol. 19, pp. 592-598.

Nakajima-Adachi et al., "Determinant analysis of IgE and IgG4 antibodies and T cells specific for bovine αS1-casein from the same patients allergic to cow's milk: Existence of αS1-casein-specific B cells and T cells characteristic in cow's-milk allergy," J. Allergy Clin. Immunol. 1998; vol. 101(5), pp. 660-671).

Rosendal et al., "Detection of Potentially Allergenic Material in 12 Hydrolyzed Milk Formulas," Journal of Dairy Science 2000, vol. 83, No. 10, abstract.

Ruiter et al., "Characterization of T cell epitopes in αs1-casein in cow's milk allergic, atopic and non-atopic children," Clin. Exp. Allergy 2006, vol. 36(3), pp. 303-310.

Ruiter et al., "Role of Human Leucocyte Antigen DQ in the Presentation of T Cell Epitopes in the Major Cow's Milk Allergen αs1-casein," Int. Arch. Allergy Immunol. 2007; vol. 143(2), pp. 119-126.

Schmidt-Weber et al., "T-cell tolerance in allergic response," Allergy 2002, vol. 57, pp. 762-768.

Schulmeister et al., "Cloning, Expression, and Mapping of Allergenic Determinants of αS1-Casein, a Major Cow's Milk Allergen," J Immunol. 2009, vol. 182(11), pp. 7019-7029.

Alles, et al., Current trends in the composition of infant milk formulas (Current Paediatrics (2004) 14, 51-63.

Brugman, S., et al., "Neonatal oral administration of DiaPep277, combined with hydrolyzed casein diet, protects against Type 1 diabetes in BB-DP rats. An experimental study," Diabetologia, vo. 47, No. 7, Jan. 1, 2004.

Brody, E., "Biological activities of bovine glycomacropeptide," British Journal of Nutrition (2000), 84, Suppl. 1, S39-S46.

Database WPI Wek 200022 Thompson Scientific, London, GB; AN 2000-251451.

Dooley, et al., http://www.medscape.com/viewarticle/449854, Dooley et al. published 2003.

Espeche Torbay, M.D., et al., "B-Casein hydrolysate generated by the cell envelope-associated proteinase of Lactobacillus delbrueckii ssp. Lactis CRL 581 protects against trinitrobenzene sulfonic acid-induced colitis in mice," J. Dairy Sci. 95:1108-1118.

Fiedorowicz, E., et al., "The influence of U-opioid receptor agonist and antagonist peptides on peripheral blood mononuclear cells (PMBCs)," Peptides 32 (2011) 707-712.

Hotta (Arterioscler Thromb Vasc Biol (Jun. 2000) 20: 1595-1599.

Knip, M., et al., "Dietary Intervention in Infancy and Later Signs of Beta-Cell Autoimmunity," New England Journal Medicine, vol. 363, pp. 1900-1908, Jan. 1, 2010.

Mao, X.Y., et al., "Free-radical-scavenging and anti-inflammatory effect of yak milk casein before and after enzymatic hydrolysis," Food Chemistry, vol. 126, No. 2, May 15, 2011.

MedlinePlus, Autoimmune Disorders, U.S. National Library of Medicine, accessed on Jan. 23, 2014.

Meisel, H., et al., "Bioactive peptides encrypted in milk proteins: proteolytic activation and thropho-functional properties," Antonie van Leenwenhqek 76:207-215, 1999.

Nakamura, Y., et al., "Metabolic diseases and pro- and prebiotics: Mechanistic insights," Nutrition & Metabolism 2012, 9:60.

(56) References Cited

OTHER PUBLICATIONS

Nielsen, D., et al., "Effect of milk hydrolysates on inflammation markers and drug-induced transcriptional alterations in cell-based models," J Anim Sci 2012, 90:403-405.

Peptide Protein Calculator, http://www.basic.northwestern.edu/biotools/proteincalc.html; downloaded on Nov. 18, 2014.

Requena, P., et al., "Bovine glycomacropeptide ameliorates experimental rat ileitis by mechanisms involving down regulation of interleukin 17," British Journal of Pharmacology (2008) 154, 825-832.

Sampson, H.A., Bernhisel-Broadbent, J., Yang, E., and Scanlon, S.M. Safety of casein hydrolysate formula in children with cow milk allergy. J. Pediatr. 1991; 118: 520-525.

Visser, J., et al., "Potential mechanisms explaining why hydrolyzed casein-based diets outclass single amino acid-based diets in the prevention of autoimmune diabetes in diabetes-prone BB rats," Diabetes Metab Res Rev 2012;28: 505-513.

Visser, J., et al., "Restoration of impaired intestinal barrier function by hydrolysed casein diet contributes to the prevention of type 1 diabetes in the diabetes-prone BioBreeding rat," Diabetologia (2010) 53:2621-2628.

Xue-Ying, M., et al., "Free-radical-scavenging and anti-inflammatory effect of yak milk casein before and after enzymatic hydrolysis," Food Chemistry 126 (2011) 484-490.

Wielinga, P., et al., "Arachidonic acid/docosahexaenoic acid-supplemented diet in early life reduces body weight gain, plasma lipids, and adiposity in later life in ApoE*3Leiden mice," Mol. Nutr. Food Res. 2012, 56, 1081-1089.

* cited by examiner

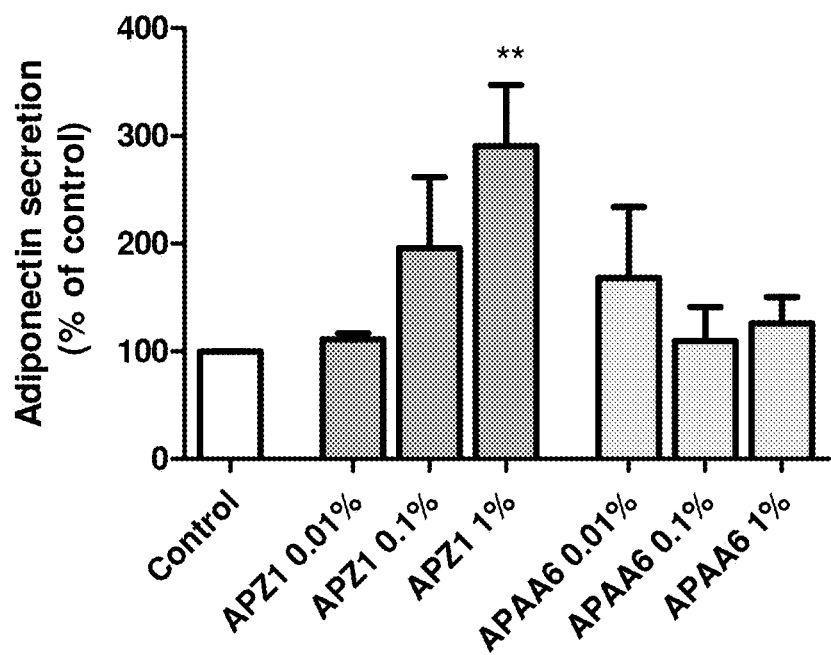

SEQUENCE LISTING

<160> NUMBER OF SEQ ID NOS: 64

<210> SEQ ID NO 1
<211> LENGTH: 8
<212> TYPE: PRT
<213> ORGANISM: Bovine

<400> SEQUENCE: 1

Ala Ile Asn Pro Ser Lys Glu Asn
1               5

<210> SEQ ID NO 2
<211> LENGTH: 5
<212> TYPE: PRT
<213> ORGANISM: BOVINE

<400> SEQUENCE: 2

Ala Pro Phe Pro Glu
1               5

<210> SEQ ID NO 3
<211> LENGTH: 6
<212> TYPE: PRT
<213> ORGANISM: BOVINE

<400> SEQUENCE: 3

Asp Ile Gly Ser Glu Ser
1               5

<210> SEQ ID NO 4
<211> LENGTH: 7
<212> TYPE: PRT
<213> ORGANISM: BOVINE

<400> SEQUENCE: 4

Asp Lys Thr Glu Ile Pro Thr
1               5

<210> SEQ ID NO 5
<211> LENGTH: 5
<212> TYPE: PRT
<213> ORGANISM: BOVINE

<400> SEQUENCE: 5

Asp Met Glu Ser Thr
1               5

<210> SEQ ID NO 6
<211> LENGTH: 4
<212> TYPE: PRT
<213> ORGANISM: BOVINE

<400> SEQUENCE: 6

Asp Met Pro Ile
1

<210> SEQ ID NO 7
<211> LENGTH: 4
<212> TYPE: PRT
<213> ORGANISM: BOVINE

<400> SEQUENCE: 7

Asp Val Pro Ser
1

<210> SEQ ID NO 8
<211> LENGTH: 7
<212> TYPE: PRT
<213> ORGANISM: BOVINE

<400> SEQUENCE: 8

Glu Thr Ala Pro Val Pro Leu
1               5

<210> SEQ ID NO 9
<211> LENGTH: 6
<212> TYPE: PRT
<213> ORGANISM: BOVINE

<400> SEQUENCE: 9

Phe Pro Gly Pro Ile Pro
1               5

<210> SEQ ID NO 10
<211> LENGTH: 7
<212> TYPE: PRT
<213> ORGANISM: BOVINE

<400> SEQUENCE: 10

Phe Pro Gly Pro Ile Pro Asn
1               5

<210> SEQ ID NO 11
<211> LENGTH: 4
<212> TYPE: PRT
<213> ORGANISM: BOVINE

<400> SEQUENCE: 11

Gly Pro Phe Pro
1

<210> SEQ ID NO 12
<211> LENGTH: 4
<212> TYPE: PRT
<213> ORGANISM: BOVINE

<400> SEQUENCE: 12

Gly Pro Ile Val
1

<210> SEQ ID NO 13
<211> LENGTH: 9
<212> TYPE: PRT
<213> ORGANISM: BOVINE

<400> SEQUENCE: 13

Ile Gly Ser Glu Ser Thr Glu Asp Gln
1               5

<210> SEQ ID NO 14
<211> LENGTH: 8
<212> TYPE: PRT
<213> ORGANISM: BOVINE

<400> SEQUENCE: 14

Ile Gly Ser Ser Ser Glu Glu Ser
1               5

<210> SEQ ID NO 15

```
<211> LENGTH: 9
<212> TYPE: PRT
<213> ORGANISM: BOVINE

<400> SEQUENCE: 15

Ile Gly Ser Ser Ser Glu Glu Ser Ala
1               5

<210> SEQ ID NO 16
<211> LENGTH: 6
<212> TYPE: PRT
<213> ORGANISM: BOVINE

<400> SEQUENCE: 16

Ile Asn Pro Ser Lys Glu
1               5

<210> SEQ ID NO 17
<211> LENGTH: 5
<212> TYPE: PRT
<213> ORGANISM: BOVINE

<400> SEQUENCE: 17

Ile Pro Asn Pro Ile
1               5

<210> SEQ ID NO 18
<211> LENGTH: 6
<212> TYPE: PRT
<213> ORGANISM: BOVINE

<400> SEQUENCE: 18

Ile Pro Asn Pro Ile Gly
1               5

<210> SEQ ID NO 19
<211> LENGTH: 9
<212> TYPE: PRT
<213> ORGANISM: BOVINE

<400> SEQUENCE: 19

Ile Pro Pro Leu Thr Gln Thr Pro Val
1               5

<210> SEQ ID NO 20
<211> LENGTH: 4
<212> TYPE: PRT
<213> ORGANISM: BOVINE

<400> SEQUENCE: 20

Ile Thr Ala Pro
1

<210> SEQ ID NO 21
<211> LENGTH: 4
<212> TYPE: PRT
<213> ORGANISM: BOVINE

<400> SEQUENCE: 21

Ile Val Pro Asn
1

<210> SEQ ID NO 22
<211> LENGTH: 7
<212> TYPE: PRT
```

-continued

<213> ORGANISM: BOVINE

<400> SEQUENCE: 22

Lys His Gln Gly Leu Pro Gln
1               5

<210> SEQ ID NO 23
<211> LENGTH: 5
<212> TYPE: PRT
<213> ORGANISM: BOVINE

<400> SEQUENCE: 23

Leu Asp Val Thr Pro
1               5

<210> SEQ ID NO 24
<211> LENGTH: 6
<212> TYPE: PRT
<213> ORGANISM: BOVINE

<400> SEQUENCE: 24

Leu Glu Asp Ser Pro Glu
1               5

<210> SEQ ID NO 25
<211> LENGTH: 5
<212> TYPE: PRT
<213> ORGANISM: BOVINE

<400> SEQUENCE: 25

Leu Pro Leu Pro Leu
1               5

<210> SEQ ID NO 26
<211> LENGTH: 6
<212> TYPE: PRT
<213> ORGANISM: BOVINE

<400> SEQUENCE: 26

Met Glu Ser Thr Glu Val
1               5

<210> SEQ ID NO 27
<211> LENGTH: 11
<212> TYPE: PRT
<213> ORGANISM: BOVINE

<400> SEQUENCE: 27

Met His Gln Pro His Gln Pro Leu Pro Pro Thr
1               5                   10

<210> SEQ ID NO 28
<211> LENGTH: 5
<212> TYPE: PRT
<213> ORGANISM: BOVINE

<400> SEQUENCE: 28

Asn Ala Val Pro Ile
1               5

<210> SEQ ID NO 29
<211> LENGTH: 5
<212> TYPE: PRT
<213> ORGANISM: BOVINE

```
<400> SEQUENCE: 29

Asn Glu Val Glu Ala
1               5

<210> SEQ ID NO 30
<211> LENGTH: 6
<212> TYPE: PRT
<213> ORGANISM: BOVINE

<400> SEQUENCE: 30

Asn Gln Glu Gln Pro Ile
1               5

<210> SEQ ID NO 31
<211> LENGTH: 5
<212> TYPE: PRT
<213> ORGANISM: BOVINE

<400> SEQUENCE: 31

Asn Val Pro Gly Glu
1               5

<210> SEQ ID NO 32
<211> LENGTH: 6
<212> TYPE: PRT
<213> ORGANISM: BOVINE

<400> SEQUENCE: 32

Pro Phe Pro Gly Pro Ile
1               5

<210> SEQ ID NO 33
<211> LENGTH: 6
<212> TYPE: PRT
<213> ORGANISM: BOVINE

<400> SEQUENCE: 33

Pro Gly Pro Ile Pro Asn
1               5

<210> SEQ ID NO 34
<211> LENGTH: 8
<212> TYPE: PRT
<213> ORGANISM: BOVINE

<400> SEQUENCE: 34

Pro His Gln Pro Leu Pro Pro Thr
1               5

<210> SEQ ID NO 35
<211> LENGTH: 5
<212> TYPE: PRT
<213> ORGANISM: BOVINE

<400> SEQUENCE: 35

Pro Ile Thr Pro Thr
1               5

<210> SEQ ID NO 36
<211> LENGTH: 4
<212> TYPE: PRT
<213> ORGANISM: BOVINE

<400> SEQUENCE: 36
```

```
Pro Asn Pro Ile
1

<210> SEQ ID NO 37
<211> LENGTH: 6
<212> TYPE: PRT
<213> ORGANISM: BOVINE

<400> SEQUENCE: 37

Pro Asn Ser Leu Pro Gln
1               5

<210> SEQ ID NO 38
<211> LENGTH: 8
<212> TYPE: PRT
<213> ORGANISM: BOVINE

<400> SEQUENCE: 38

Pro Gln Leu Glu Ile Val Pro Asn
1               5

<210> SEQ ID NO 39
<211> LENGTH: 7
<212> TYPE: PRT
<213> ORGANISM: BOVINE

<400> SEQUENCE: 39

Pro Gln Asn Ile Pro Pro Leu
1               5

<210> SEQ ID NO 40
<211> LENGTH: 6
<212> TYPE: PRT
<213> ORGANISM: BOVINE

<400> SEQUENCE: 40

Pro Val Leu Gly Pro Val
1               5

<210> SEQ ID NO 41
<211> LENGTH: 4
<212> TYPE: PRT
<213> ORGANISM: BOVINE

<400> SEQUENCE: 41

Pro Val Pro Gln
1

<210> SEQ ID NO 42
<211> LENGTH: 5
<212> TYPE: PRT
<213> ORGANISM: BOVINE

<400> SEQUENCE: 42

Pro Val Val Val Pro
1               5

<210> SEQ ID NO 43
<211> LENGTH: 6
<212> TYPE: PRT
<213> ORGANISM: BOVINE

<400> SEQUENCE: 43

Pro Val Val Val Pro Pro
1               5
```

```
<210> SEQ ID NO 44
<211> LENGTH: 11
<212> TYPE: PRT
<213> ORGANISM: BOVINE

<400> SEQUENCE: 44

Ser Ile Gly Ser Ser Ser Glu Glu Ser Ala Glu
1               5                   10

<210> SEQ ID NO 45
<211> LENGTH: 7
<212> TYPE: PRT
<213> ORGANISM: BOVINE

<400> SEQUENCE: 45

Ser Ile Ser Ser Ser Glu Glu
1               5

<210> SEQ ID NO 46
<211> LENGTH: 11
<212> TYPE: PRT
<213> ORGANISM: BOVINE

<400> SEQUENCE: 46

Ser Ile Ser Ser Ser Glu Glu Ile Val Pro Asn
1               5                   10

<210> SEQ ID NO 47
<211> LENGTH: 7
<212> TYPE: PRT
<213> ORGANISM: BOVINE

<400> SEQUENCE: 47

Ser Lys Asp Ile Gly Ser Glu
1               5

<210> SEQ ID NO 48
<211> LENGTH: 6
<212> TYPE: PRT
<213> ORGANISM: BOVINE

<400> SEQUENCE: 48

Ser Pro Pro Glu Ile Asn
1               5

<210> SEQ ID NO 49
<211> LENGTH: 7
<212> TYPE: PRT
<213> ORGANISM: BOVINE

<400> SEQUENCE: 49

Ser Pro Pro Glu Ile Asn Thr
1               5

<210> SEQ ID NO 50
<211> LENGTH: 7
<212> TYPE: PRT
<213> ORGANISM: BOVINE

<400> SEQUENCE: 50

Thr Asp Ala Pro Ser Phe Ser
1               5
```

```
<210> SEQ ID NO 51
<211> LENGTH: 5
<212> TYPE: PRT
<213> ORGANISM: BOVINE

<400> SEQUENCE: 51

Thr Glu Asp Glu Leu
1               5

<210> SEQ ID NO 52
<211> LENGTH: 6
<212> TYPE: PRT
<213> ORGANISM: BOVINE

<400> SEQUENCE: 52

Val Ala Thr Glu Glu Val
1               5

<210> SEQ ID NO 53
<211> LENGTH: 5
<212> TYPE: PRT
<213> ORGANISM: BOVINE

<400> SEQUENCE: 53

Val Leu Pro Val Pro
1               5

<210> SEQ ID NO 54
<211> LENGTH: 4
<212> TYPE: PRT
<213> ORGANISM: BOVINE

<400> SEQUENCE: 54

Val Pro Gly Glu
1

<210> SEQ ID NO 55
<211> LENGTH: 6
<212> TYPE: PRT
<213> ORGANISM: BOVINE

<400> SEQUENCE: 55

Val Pro Gly Glu Ile Val
1               5

<210> SEQ ID NO 56
<211> LENGTH: 6
<212> TYPE: PRT
<213> ORGANISM: BOVINE

<400> SEQUENCE: 56

Val Pro Ile Thr Pro Thr
1               5

<210> SEQ ID NO 57
<211> LENGTH: 4
<212> TYPE: PRT
<213> ORGANISM: BOVINE

<400> SEQUENCE: 57

Val Pro Ser Glu
1

<210> SEQ ID NO 58
<211> LENGTH: 9
```

-continued

```
<212> TYPE: PRT
<213> ORGANISM: BOVINE

<400> SEQUENCE: 58

Val Val Pro Pro Phe Leu Gln Pro Glu
1               5

<210> SEQ ID NO 59
<211> LENGTH: 5
<212> TYPE: PRT
<213> ORGANISM: BOVINE

<400> SEQUENCE: 59

Val Val Val Pro Pro
1               5

<210> SEQ ID NO 60
<211> LENGTH: 6
<212> TYPE: PRT
<213> ORGANISM: BOVINE

<400> SEQUENCE: 60

Tyr Pro Phe Pro Gly Pro
1               5

<210> SEQ ID NO 61
<211> LENGTH: 8
<212> TYPE: PRT
<213> ORGANISM: BOVINE

<400> SEQUENCE: 61

Tyr Pro Phe Pro Gly Pro Ile Pro
1               5

<210> SEQ ID NO 62
<211> LENGTH: 9
<212> TYPE: PRT
<213> ORGANISM: BOVINE

<400> SEQUENCE: 62

Tyr Pro Phe Pro Gly Pro Ile Pro Asn
1               5

<210> SEQ ID NO 63
<211> LENGTH: 5
<212> TYPE: PRT
<213> ORGANISM: BOVINE

<400> SEQUENCE: 63

Tyr Pro Ser Gly Ala
1               5

<210> SEQ ID NO 64
<211> LENGTH: 5
<212> TYPE: PRT
<213> ORGANISM: BOVINE

<400> SEQUENCE: 64

Tyr Pro Val Glu Pro
1               5
```

US 9,345,741 B2

NUTRITIONAL COMPOSITION CONTAINING A PEPTIDE COMPONENT WITH ADIPONECTIN SIMULATING PROPERTIES AND USES THEREOF

TECHNICAL FIELD

The present disclosure relates nutritional compositions that include a peptide component that may promote maintaining a healthy body weight. More specifically the nutritional composition may promote a health body weight by stimulating adiponectin production in a target subject. The nutritional compositions described herein are suitable for administration to adult and pediatric subjects.

Additionally, the present disclosure provides methods maintaining healthy body weight by providing the nutritional composition comprising the peptide component disclosed herein to a target subject. Further disclosed herein are methods for stimulating adiponectin production and/or enhancing adiponectin levels by providing the nutritional composition including the peptide component described herein to a target subject.

BACKGROUND

Obesity, especially childhood obesity is an increasing problem in developing countries. For example, in the United Stated in the year 2000 approximately 15% of children, up to age 11, were considered to be obese, whereas in 1980 only 7% were considered obese. Moreover, children who develop obesity are very likely to have obesity persist into adulthood.

Obesity is characterized by an accumulated increase in body fat and increases the likelihood of various diseases including, but not limited to, coronary heart disease, type 2 diabetes mellitus, obstructive sleep apnea, respiratory problems, cancers, including endometrial, breast and colon, hypertension, dyslipidemia, for example high total cholesterol and/or high levels of triglycerides, stroke, liver disease, gallbladder disease, and osteoarthritis.

Adiponectin (also called ACRP30, adipoQ or GBP28), is a protein hormone produced by adipocytes in adipose tissue, as well as the placenta during pregnancy. Adiponectin has several beneficial and protective effects, including anti-inflammatory, vasculoprotective and anti-diabetic effects. Moreover, adiponectin modulates several metabolic processes that may impact human development. For example, adiponectin is involved in regulating glucose levels as well as fatty acid metabolism, and is inversely correlated with body fat percentage in adults. In children, similar associations with body mass index and insulin resistance have been reported.

High concentrations of circulating adiponectin have positive health effects, at least in part due to the reduction of proinflammatory cytokines, improvement of insulin sensitivity, and an increase in fatty acid metabolism. In humans, adiponectin levels are inversely correlated with insulin resistance independent of adiposity, with the lowest levels of adiponectin in individuals with type 2 diabetes. Furthermore, low adiponectin precedes the development of insulin resistance, suggesting a direct effect of adiponectin on insulin sensitivity. Mouse studies have confirmed that adiponectin improves glucose utilization. High adiponectin has also been associated with an anti-atherogenic lipid profile.

Adiponectin is further inversely correlated with plasma triglycerides and positively correlated with plasma high density lipoprotein cholesterol levels. Adiponectin directly influences lipid metabolism and oxidation. Additionally, adiponectin has strong anti-inflammatory properties. Adiponectin decreases TNF alpha and IL-6 production, and increases expression of anti-inflammatory cytokines in macrophages. Adiponectin also works downstream of TNF-a to suppress its ability to activate the NF-kb pathway. Adiponectin inhibits the formation of granulocyte-macrophage colonies in vivo, and inhibits the phagocytic activity of mature macrophages.

Thus, it would useful to provide nutritional compositions or medical foods that are able to increase the production of adiponectin in a subject. In particular, it may be useful to improve adiponectin levels in early life in order to reduce or prevent adult metabolic diseases.

Accordingly, the present disclosure provides a nutritional composition including a protein equivalent source comprising a peptide component including the following peptides: SEQ ID NO 4, SEQ ID NO 13, SEQ ID NO 17, SEQ ID NO 21, SEQ ID NO 24, SEQ ID NO 30, SEQ ID NO 31, SEQ ID NO 32, SEQ ID NO 51, SEQ ID NO 57, SEQ ID NO 60, and SEQ ID NO 63. In some embodiments, the peptide component comprises at least 10 additional peptides selected from Table 1.

In some embodiments the peptide component may comprise at least 5 peptides selected from Table 1 and at least 3 additional peptides selected from Table 2. In still other embodiments, the peptide component may comprise at least 10 additional peptides selected from Table 1.

Without being bound by any particular theory, it is believed that the peptide component described herein may have favorable effects on adiponectin levels when consumed by individuals. Moreover, the present disclosure includes methods for stimulating adiponectin production by providing a nutritional composition including the peptide component disclosed herein.

Additionally, the present disclosure is directed to methods for promoting and/or maintaining a healthy body weight by stimulating adiponectin production in a target subject, the method comprising providing a nutritional composition including the peptide component disclosed herein to a target subject.

BRIEF SUMMARY

Briefly, the present disclosure is directed, in an embodiment, to a nutritional composition comprising a peptide component including the following peptides: SEQ ID NO 4, SEQ ID NO 13, SEQ ID NO 17, SEQ ID NO 21, SEQ ID NO 24, SEQ ID NO 30, SEQ ID NO 31, SEQ ID NO 32, SEQ ID NO 51, SEQ ID NO 57, SEQ ID NO 60, and SEQ ID NO 63. In some embodiments, the peptide component may comprise at least 10 additional peptides selected from Table 1.

In some embodiments the peptide component may comprise at least 5 peptides selected from Table 1 and at least 3 peptides selected from Table 2. In still other embodiments, the peptide component may comprise at least 10 additional peptides selected from Table 1.

In some embodiments the nutritional composition includes a protein equivalent source wherein 20% to 80% of the protein equivalent source comprises the peptide component described herein and 20% to 80% of the peptide component comprises intact protein, hydrolyzed protein, including a partially hydrolyzed protein, and combinations thereof.

The nutritional composition(s) of the present disclosure may further comprise an infant formula. In some embodiments, the nutritional composition(s) of the present disclosure may comprise a pediatric nutritional composition, nutritional supplement, nutritional additive or adult nutritional composition.

In some embodiments the disclosure is directed to a method for maintaining a healthy body weight by providing the nutritional composition including the peptide component disclosed herein. Further the disclosure provides method(s) for stimulating adiponectin production in a target subject, the method includes providing a nutritional composition including the peptide component disclosed herein. In some embodiments the present disclosure provides methods for maintaining a healthy body weight by stimulating adiponectin comprising administering the nutritional composition including the peptide component described herein.

It is to be understood that both the foregoing general description and the following detailed description present embodiments of the disclosure and are intended to provide an overview or framework for understanding the nature and character of the disclosure as it is claimed. The description serves to explain the principles and operations of the claimed subject matter. Other and further features and advantages of the present disclosure will be readily apparent to those skilled in the art upon a reading of the following disclosure.

BRIEF DESCRIPTION OF THE DRAWINGS

FIG. 1 shows adiponection secretion of subcutaneous tissue after exposure to casein hydrolysate.

DETAILED DESCRIPTION

Reference now will be made in detail to the embodiments of the present disclosure, one or more examples of which are set forth hereinbelow. Each example is provided by way of explanation of the nutritional composition of the present disclosure and is not a limitation. In fact, it will be apparent to those skilled in the art that various modifications and variations can be made to the teachings of the present disclosure without departing from the scope of the disclosure. For instance, features illustrated or described as part of one embodiment, can be used with another embodiment to yield a still further embodiment.

Thus, it is intended that the present disclosure covers such modifications and variations as come within the scope of the appended claims and their equivalents. Other objects, features and aspects of the present disclosure are disclosed in or are apparent from the following detailed description. It is to be understood by one of ordinary skill in the art that the present discussion is a description of exemplary embodiments only and is not intended as limiting the broader aspects of the present disclosure.

The present disclosure relates generally to nutritional compositions comprising a protein equivalent source, which includes the peptides disclosed herein as SEQ ID NO 4, SEQ ID NO 13, SEQ ID NO 17, SEQ ID NO 21, SEQ ID NO 24, SEQ ID NO 30, SEQ ID NO 31, SEQ ID NO 32, SEQ ID NO 51, SEQ ID NO 57, SEQ ID NO 60, and SEQ ID NO 63. In some embodiments, the peptide component may comprise at least 10 additional peptides disclosed in Table 1.

In some embodiments 20% to 80% of the protein equivalent source comprises the peptide component described herein and 20% to 80% of the protein equivalent source comprises an intact protein, a partially hydrolyzed protein, and combinations thereof.

Additionally, the disclosure relates to methods of maintaining a healthy body weight by providing a target subject a nutritional composition containing the peptide component described herein. Further, the disclosure related to methods of maintaining a healthy bodyweight by stimulating adiponectin levels by providing a nutritional composition including the peptide component disclosed herein to a target subject.

When administered to individuals, the peptide component has advantageous effects on metabolism and the inflammatory response. More specifically, the peptide component is capable of increasing adiponectin production. While not being bound by any particular theory, increased adiponectin has several beneficial and protective effects, including anti-inflammatory, vasculoprotective, and anti-diabetic effects. For example, in some embodiments, the peptide component reduces total cholesterol levels. In certain embodiments, the peptide component reduces low-density lipoprotein cholesterol (LDL), and more particularly, in some embodiments, the peptide component promotes a healthy ratio of total cholesterol to high density lipoprotein (HDL) cholesterol. For example, a ratio of 5:1 or less is considered healthy, and a ratio of about 3.5:1 is ideal.

In some embodiments, the peptide component promotes a healthy body weight and/or a healthy body fat mass in a subject. A healthy body weight can be evaluated by calculating a subject's body mass index (BMI), where a BMI of about 18.5 to about 25 for an adult is considered healthy. Body fat is often assessed as body fat percentage, where women of normal health have a body fat percentage ranging from about 21 to about 31%, and men of normal health have a body fat ranging from about 14 to about 24%. These values also may vary depending on a subject's age, where a healthy body fat percentage is somewhat higher in elderly subjects.

"Nutritional composition" means a substance or formulation that satisfies at least a portion of a subject's nutrient requirements. The terms "nutritional(s)", "nutritional formula (s)", "enteral nutritional(s)", and "nutritional supplement(s)" are used as non-limiting examples of nutritional composition(s) throughout the present disclosure. Moreover, "nutritional composition(s)" may refer to liquids, powders, gels, pastes, solids, concentrates, suspensions, or ready-to-use forms of enteral formulas, oral formulas, formulas for infants, formulas for pediatric subjects, formulas for children, growing-up milks and/or formulas for adults. The term "enteral" means deliverable through or within the gastrointestinal, or digestive, tract. "Enteral administration" includes oral feeding, intragastric feeding, transpyloric administration, or any other administration into the digestive tract. "Administration" is broader than "enteral administration" and includes parenteral administration or any other route of administration by which a substance is taken into a subject's body.

The term "medical food" refers enteral compositions that are formulated or intended for the dietary management of a disease or disorder. A medical food may be a food for oral ingestion or tube feeding (nasogastric tube), may be labeled for the dietary management of a specific medical disorder, disease or condition for which there are distinctive nutritional requirements, and may be intended to be used under medical supervision.

The term "peptide" as used herein describes linear molecular chains of amino acids, including single chain molecules or their fragments. The peptides described herein, include no more than 50 total amino acids. Peptides may further form oligomers or multimers consisting of at least two identical or different molecules. Furthermore, peptidomimetics of such peptides where amino acid(s) and/or peptide bond(s) have been replaced by functional analogs are also encompassed by the term "peptide". Such functional analogues may include, but are not limited to, all known amino acids other than the 20 gene-encoded amino acids such as selenocysteine.

The term "peptide" may also refer to naturally modified peptides where the modification is effected, for example, by glycosylation, acetylation, phosphorylation and similar modification which are well known in the art. In some embodiments, the peptide component is distinguished from a protein source also disclosed herein. Further, peptides may, for example, be produced recombinantly, semi-synthetically, synthetically, or obtained from natural sources such as after hydrolysation of proteins, including but not limited to casein, all according to methods known in the art.

The term "degree of hydrolysis" refers to the extent to which peptide bonds are broken by a hydrolysis method. For example, the protein equivalent source of the present disclosure may, in some embodiments comprise a protein having a degree of hydrolysis of no greater than 40%.

The term "partially hydrolyzed" means having a degree of hydrolysis which is greater than 0% but less than 50%.

The term "extensively hydrolyzed" means having a degree of hydrolysis which is greater than or equal to 50%.

The term "molar mass distribution" when used in reference to a hydrolyzed protein or protein hydrolysate pertains to the molar mass of each peptide present in the protein hydrolysate. For example, a protein hydrolysate having a molar mass distribution of greater than 500 Daltons means that each peptide included in the protein hydrolysate has a molar mass of at least 500 Daltons. Accordingly, in some embodiments, the peptides disclosed in Table 1 and Table 2 are derived from a protein hydrolysate having a molar mass distribution of greater than 500 Daltons. To produce a protein hydrolysate having a molar mass distribution of greater than 500 Daltons, a protein hydrolysate may be subjected to certain filtering procedures or any other procedure known in the art for removing peptides, amino acids, and/or other proteinaceous material having a molar mass of less than 500 Daltons. For the purposes of this disclosure, any method known in the art may be used to produce the protein hydrolysate having a molar mass distribution of greater than 500 Dalton.

The term "protein equivalent" or "protein equivalent source" includes any protein source, such as soy, egg, whey, or casein, as well as non-protein sources, such as peptides or amino acids. Further, the protein equivalent source can be any used in the art, e.g., nonfat milk, whey protein, casein, soy protein, hydrolyzed protein, amino acids, and the like. Bovine milk protein sources useful in practicing the present disclosure include, but are not limited to, milk protein powders, milk protein concentrates, milk protein isolates, nonfat milk solids, nonfat milk, nonfat dry milk, whey protein, whey protein isolates, whey protein concentrates, sweet whey, acid whey, casein, acid casein, caseinate (e.g. sodium caseinate, sodium calcium caseinate, calcium caseinate), soy bean proteins, and any combinations thereof. The protein equivalent source can, in some embodiments comprise hydrolyzed protein, including partially hydrolyzed protein and extensively hydrolyzed protein. The protein equivalent source may, in some embodiments, include intact protein.

The term "protein equivalent source" also encompasses free amino acids. In some embodiments, the amino acids may comprise, but are not limited to, histidine, isoleucine, leucine, lysine, methionine, cysteine, phenylalanine, tyrosine, threonine, tryptophan, valine, alanine, arginine, asparagine, aspartic acid, glutamic acid, glutamine, glycine, proline, serine, carnitine, taurine and mixtures thereof. In some embodiments, the amino acids may be branched chain amino acids. In certain other embodiments, small amino acid peptides may be included as the protein component of the nutritional composition. Such small amino acid peptides may be naturally occurring or synthesized.

"Pediatric subject" means a human less than 13 years of age. In some embodiments, a pediatric subject refers to a human subject that is between birth and 8 years old. In other embodiments, a pediatric subject refers to a human subject between 1 and 6 years of age. In still further embodiments, a pediatric subject refers to a human subject between 6 and 12 years of age. The term "pediatric subject" may refer to infants (preterm or fullterm) and/or children, as described below.

"Infant" means a human subject ranging in age from birth to not more than one year and includes infants from 0 to 12 months corrected age. The phrase "corrected age" means an infant's chronological age minus the amount of time that the infant was born premature. Therefore, the corrected age is the age of the infant if it had been carried to full term. The term infant includes low birth weight infants, very low birth weight infants, and preterm infants. "Preterm" means an infant born before the end of the $37^{th}$ week of gestation. "Full term" means an infant born after the end of the $37^{th}$ week of gestation.

"Child" means a subject ranging in age from 12 months to about 13 years. In some embodiments, a child is a subject between the ages of 1 and 12 years old. In other embodiments, the terms "children" or "child" refer to subjects that are between one and about six years old, or between about seven and about 12 years old. In other embodiments, the terms "children" or "child" refer to any range of ages between 12 months and about 13 years.

"Children's nutritional product" refers to a composition that satisfies at least a portion of the nutrient requirements of a child. A growing-up milk is an example of a children's nutritional product.

"Infant formula" means a composition that satisfies at least a portion of the nutrient requirements of an infant. In the United States, the content of an infant formula is dictated by the federal regulations set forth at 21 C.F.R. Sections 100, 106, and 107. These regulations define macronutrient, vitamin, mineral, and other ingredient levels in an effort to simulate the nutritional and other properties of human breast milk.

The term "growing-up milk" refers to a broad category of nutritional compositions intended to be used as a part of a diverse diet in order to support the normal growth and development of a child between the ages of about 1 and about 6 years of age.

"Nutritionally complete" means a composition that may be used as the sole source of nutrition, which would supply essentially all of the required daily amounts of vitamins, minerals, and/or trace elements in combination with proteins, carbohydrates, and lipids. Indeed, "nutritionally complete" describes a nutritional composition that provides adequate amounts of carbohydrates, lipids, essential fatty acids, proteins, essential amino acids, conditionally essential amino acids, vitamins, minerals and energy required to support normal growth and development of a subject.

Therefore, a nutritional composition that is "nutritionally complete" for a preterm infant will, by definition, provide qualitatively and quantitatively adequate amounts of carbohydrates, lipids, essential fatty acids, proteins, essential amino acids, conditionally essential amino acids, vitamins, minerals, and energy required for growth of the preterm infant.

A nutritional composition that is "nutritionally complete" for a full term infant will, by definition, provide qualitatively and quantitatively adequate amounts of all carbohydrates, lipids, essential fatty acids, proteins, essential amino acids, conditionally essential amino acids, vitamins, minerals, and energy required for growth of the full term infant.

A nutritional composition that is "nutritionally complete" for a child will, by definition, provide qualitatively and quantitatively adequate amounts of all carbohydrates, lipids, essential fatty acids, proteins, essential amino acids, conditionally essential amino acids, vitamins, minerals, and energy required for growth of a child.

As applied to nutrients, the term "essential" refers to any nutrient that cannot be synthesized by the body in amounts sufficient for normal growth and to maintain health and that, therefore, must be supplied by the diet. The term "conditionally essential" as applied to nutrients means that the nutrient must be supplied by the diet under conditions when adequate amounts of the precursor compound is unavailable to the body for endogenous synthesis to occur.

"Prebiotic" means a non-digestible food ingredient that beneficially affects the host by selectively stimulating the growth and/or activity of one or a limited number of bacteria in the digestive tract that can improve the health of the host.

"Probiotic" means a microorganism with low or no pathogenicity that exerts at least one beneficial effect on the health of the host.

The term "inactivated probiotic" means a probiotic wherein the metabolic activity or reproductive ability of the referenced probiotic organism has been reduced or destroyed. The "inactivated probiotic" does, however, still retain, at the cellular level, at least a portion its biological glycol-protein and DNA/RNA structure. As used herein, the term "inactivated" is synonymous with "non-viable". More specifically, a non-limiting example of an inactivated probiotic is inactivated *Lactobacillus rhamnosus* GG ("LGG") or "inactivated LGG".

All percentages, parts and ratios as used herein are by weight of the total formulation, unless otherwise specified.

The nutritional composition of the present disclosure may be substantially free of any optional or selected ingredients described herein, provided that the remaining nutritional composition still contains all of the required ingredients or features described herein. In this context, and unless otherwise specified, the term "substantially free" means that the selected composition may contain less than a functional amount of the optional ingredient, typically less than 0.1% by weight, and also, including zero percent by weight of such optional or selected ingredient.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional ingredients, components or limitations described herein or otherwise useful in nutritional compositions.

As used herein, the term "about" should be construed to refer to both of the numbers specified as the endpoint(s) of any range. Any reference to a range should be considered as providing support for any subset within that range.

Obesity is a medical condition in which excess body fat has accumulated to such an extent that is causes an adverse effect on health. For example, obesity can lead to reduced life expectancy, heart disease, type 2 diabetes mellitus, obstructive sleep apnea and osteoarthritis. Experts hypothesize that obesity is one of the leading preventable causes of death worldwide, and has increasing prevalence in adults and children. Adiponectin is involved in regulating glucose levels as well as fatty acid metabolism, and is inversely correlated with body fat percentage in adults.

Accordingly, the present disclosure relates generally to nutritional compositions comprising a protein equivalent source, wherein the protein equivalent source includes a peptide component comprising SEQ ID NO 4, SEQ ID NO 13, SEQ ID NO 17, SEQ ID NO 21, SEQ ID NO 24, SEQ ID NO 30, SEQ ID NO 31, SEQ ID NO 32, SEQ ID NO 51, SEQ ID NO 57, SEQ ID NO 60, and SEQ ID NO 63. In some embodiments, the peptide component may comprise additional peptides disclosed in Table 1. For example, the composition may include at least 10 additional peptides disclosed in Table 1. In some embodiments, 20% to 80% of the protein equivalent source comprises the peptide component, and 20% to 80% of the protein equivalent source comprises an intact protein, a partially hydrolyzed protein, and combinations thereof. In some embodiments, the term "additional" means selecting different peptides than those enumerated.

In another embodiment 20% to 80% of the protein equivalent source includes a peptide component comprising at least 3 peptides selected from the group consisting of SEQ ID NO 4, SEQ ID NO 13, SEQ ID NO 17, SEQ ID NO 21, SEQ ID NO 24, SEQ ID NO 30, SEQ ID NO 31, SEQ ID NO 32, SEQ ID NO 51, SEQ ID NO 57, SEQ ID NO 60, and SEQ ID NO 63, and at least 5 additional peptides selected from Table 1; and wherein 20% to 80% of the protein equivalent source comprises an intact protein, a partially hydrolyzed protein, or combinations thereof.

Without being bound by any particular theory, providing a nutritional composition including the peptide component of the present disclosure may favorably enhance adiponectin levels thus promoting the maintenance of a healthy body weight in a target subject.

Table 1 below identifies the specific amino acid sequences that may be included in the peptide component of the nutritional composition.

TABLE 1

| Seq ID | Amino Acid Sequence | (aa) |
|---|---|---|
| 1 | Ala Ile Asn Pro Ser Lys Glu Asn | 8 |
| 2 | Ala Pro Phe Pro Glu | 5 |
| 3 | Asp Ile Gly Ser Glu Ser | 6 |
| 4 | Asp Lys Thr Glu Ile Pro Thr | 7 |
| 5 | Asp Met Glu Ser Thr | 5 |
| 6 | Asp Met Pro Ile | 4 |
| 7 | Asp Val Pro Ser | 4 |
| n/a | Glu Asp Ile | 3 |
| n/a | Glu Leu Phe | 3 |
| n/a | Glu Met Pro | 3 |
| 8 | Glu Thr Ala Pro Val Pro Leu | 7 |
| 9 | Phe Pro Gly Pro Ile Pro | 6 |
| 10 | Phe Pro Gly Pro Ile Pro Asn | 7 |
| 11 | Gly Pro Phe Pro | 4 |

TABLE 1-continued

| Seq ID | Amino Acid Sequence | (aa) |
|---|---|---|
| 12 | Gly Pro Ile Val | 4 |
| 13 | Ile Gly Ser Glu Ser Thr Glu Asp Gln | 9 |
| 14 | Ile Gly Ser Ser Ser Glu Glu Ser | 8 |
| 15 | Ile Gly Ser Ser Ser Glu Glu Ser Ala | 9 |
| 16 | Ile Asn Pro Ser Lys Glu | 6 |
| 17 | Ile Pro Asn Pro Ile | 5 |
| 18 | Ile Pro Asn Pro Ile Gly | 6 |
| 19 | Ile Pro Pro Leu Thr Gln Thr Pro Val | 9 |
| 20 | Ile Thr Ala Pro | 4 |
| 21 | Ile Val Pro Asn | 4 |
| 22 | Lys His Gln Gly Leu Pro Gln | 7 |
| 23 | Leu Asp Val Thr Pro | 5 |
| 24 | Leu Glu Asp Ser Pro Glu | 6 |
| 25 | Leu Pro Leu Pro Leu | 5 |
| 26 | Met Glu Ser Thr Glu Val | 6 |
| 27 | Met His Gln Pro His Gln Pro Leu Pro Pro Thr | 11 |
| 28 | Asn Ala Val Pro Ile | 5 |
| 29 | Asn Glu Val Glu Ala | 5 |
| n/a | Asn Leu Leu | 3 |
| 30 | Asn Gln Glu Gln Pro Ile | 6 |
| 31 | Asn Val Pro Gly Glu | 5 |
| 32 | Pro Phe Pro gly Pro Ile | 6 |
| 33 | Pro Gly Pro Ile Pro Asn | 6 |
| 34 | Pro His Gln Pro Leu Pro Pro Thr | 8 |
| 35 | Pro Ile Thr Pro Thr | 5 |
| 36 | Pro Asn Pro Ile | 4 |
| 37 | Pro Asn Ser Leu Pro Gln | 6 |
| 38 | Pro Gln Leu Glu Ile Val Pro Asn | 8 |
| 39 | Pro Gln Asn Ile Pro Pro Leu | 7 |
| 40 | Pro Val Leu Gly Pro Val | 6 |
| 41 | Pro Val Pro Gln | 4 |
| 42 | Pro Val Val Val Pro | 5 |
| 43 | Pro Val Val Val Pro Pro | 6 |
| 44 | Ser Ile Gly Ser Ser Ser Glu Glu Ser Ala Glu | 11 |
| 45 | Ser Ile Ser Ser Ser Glu Glu | 7 |
| 46 | Ser Ile Ser Ser Ser Glu Glu Ile Val Pro Asn | 11 |
| 47 | Ser Lys Asp Ile Gly Ser Glu | 7 |

TABLE 1-continued

| Seq ID | Amino Acid Sequence | (aa) |
|---|---|---|
| 48 | Ser Pro Pro Glu Ile Asn | 6 |
| 49 | Ser Pro Pro Glu Ile Asn Thr | 7 |
| 50 | Thr Asp Ala Pro Ser Phe Ser | 7 |
| 51 | Thr Glu Asp Glu Leu | 5 |
| 52 | Val Ala Thr Glu Glu Val | 6 |
| 53 | Val Leu Pro Val Pro | 5 |
| 54 | Val Pro Gly Glu | 4 |
| 55 | Val Pro Gly Glu Ile Val | 6 |
| 56 | Val Pro Ile Thr Pro Thr | 6 |
| 57 | Val Pro Ser Glu | 4 |
| 58 | Val Val Pro Pro Phe Leu Gln Pro Glu | 9 |
| 59 | Val Val Val Pro Pro | 5 |
| 60 | Tyr Pro Phe Pro Gly Pro | 6 |
| 61 | Tyr Pro Phe Pro Gly Pro Ile Pro | 8 |
| 62 | Tyr Pro Phe Pro Gly Pro Ile Pro Asn | 9 |
| 63 | Tyr Pro Ser Gly Ala | 5 |
| 64 | Tyr Pro Val Glu Pro | 5 |

Table 2 below further identifies a subset of amino acid sequences from Table 1 that may be included and/or comprise the peptide component disclosed herein.

TABLE 2

| Seq ID | Amino Acid Sequence | (aa) |
|---|---|---|
| 4 | Asp Lys Thr Glu Ile Pro Thr | 7 |
| 13 | Ile Gly Ser Glu Ser Thr Glu Asp Gln | 9 |
| 17 | Ile Pro Asn Pro Ile Gly | 6 |
| 21 | Ile Val Pro Asn | 4 |
| 24 | Leu Glu Asp Ser Pro Glu | 6 |
| 30 | Asn Gln Glu Gln Pro Ile | 6 |
| 31 | Asn Val Pro Gly Glu | 5 |
| 32 | Pro Phe Pro Gly Pro Ile | 6 |
| 51 | Thr Glu Asp Glu Leu | 5 |
| 57 | Val Pro Ser Glu | 4 |
| 60 | Tyr Pro Phe Pro Gly Pro | 6 |
| 63 | Tyr Pro Ser Gly Ala | 5 |

In some embodiments, the peptide component may be present in the nutritional composition in an amount from about 0.2 g/100 kcal to about 5.6 g/100 kcal. In other embodiments the peptide component may be present in the nutritional composition in an amount from about 1 g/100 kcal to about 4 g/100 kcal. In still other embodiments, the peptide component may be present in the nutritional composition in an amount from about 2 g/100 kcal to about 3 g/100 kcal.

The peptide component disclosed herein, may be formulated with other ingredients in the nutritional composition to provide appropriate nutrient levels for the target subject. In some embodiments, the peptide component is included in a nutritionally complete formula that is suitable to support normal growth.

In other embodiments, the peptide component may comprise a nutritional supplement or additive that may be added to other nutritional formulations including, but not limited to, foodstuffs and/or beverages. For the purposes of this disclosure, "nutritional supplement" includes a concentrated source of nutrient, for example the peptides identified herein, or alternatively other substances with a nutritional or physiological effective whose purpose is to supplement the normal diet.

The peptide component may be provided by as an element of a protein equivalent source. In some embodiments, the peptides identified in Tables 1 and 2, may be provided by a protein equivalent source obtained from cow's milk proteins, including but not limited to bovine casein and bovine whey. In some embodiments, the protein equivalent source comprises hydrolyzed bovine casein or hydrolyzed bovine whey. Accordingly, in some embodiments, the peptides identified in Table 1 and Table 2 may be provided by a casein hydrolysate. Such peptides may be obtained by hydrolysis or may be synthesized in vitro by methods know to the skilled person. A nonlimiting example of a method of hydrolysis utilizing a proteolytic enzyme is disclosed in U.S. Pat. No. 7,618,669 to Rangavajla et al., which is hereby incorporated by reference in its entirety however, other methods of hydrolysis may be used in practice of the present disclosure.

In some embodiments, the protein equivalent source comprises a hydrolyzed protein, such as casein, which includes partially hydrolyzed protein and extensively hydrolyzed protein. In some embodiments, the protein equivalent source comprises a hydrolyzed protein including peptides having a molar mass distribution of greater than 500 Daltons. In some embodiments, they hydrolyzed protein comprises peptides having a molar mass distribution in the range of from about 500 Daltons to about 1,500 Daltons. Still, in some embodiments the hydrolyzed protein may comprise peptides having a molar mass distribution range of from about 500 Daltons to about 2,000 Daltons.

In some embodiments, the protein equivalent source may comprise the peptide component, intact protein, hydrolyzed protein, including partially hydrolyzed protein, and combinations thereof. In some embodiments, 20% to 80% of the protein equivalent source comprises the peptide component disclosed herein. In some embodiments, 40% to 70% of the protein equivalent source comprises the peptide component disclosed herein. In still other embodiments, 50% to 60% of the protein equivalent source comprises the peptide component.

In some embodiments, 20% to 80% of the protein equivalent source comprises intact protein, partially hydrolyzed protein, or combinations thereof. In some embodiments, 30% to 60% of the protein equivalent source comprises intact proteins, partially hydrolyzed proteins, or a combination thereof. In still further embodiments, 40% to 50% of the protein equivalent source may comprise intact proteins, partially hydrolyzed protein, or a combination thereof.

In some embodiments the protein equivalent source comprises partially hydrolyzed protein having a degree of hydrolysis of less than 40%. In still other embodiments, the protein equivalent source may comprise partially hydrolyzed protein having a degree of hydrolysis of less than 25%, or less than 15%.

In some embodiments, the nutritional composition comprises between about 1 g and about 7 g of a protein equivalent source per 100 kcal. In other embodiments, the nutritional composition comprises between about 3.5 g and about 4.5 g of protein equivalent source per 100 kcal.

Additionally, the peptide component may be added or incorporated into the nutritional composition by any method well known in the art. In some embodiments, the peptide component may be added to a nutritional composition to supplement the nutritional composition. For example, in one embodiment, the peptide component may be added to a commercially available infant formula. For example, Enfalac, Enfamil®, Enfamil® Premature Formula, Enfamil® with Iron, Enfamil® LIPIL®, Lactofree®, Nutramigen®, Pregestimil®, and ProSobee® (available from Mead Johnson & Company, Evansville, Ind., U.S.A.) may be supplemented with suitable levels of the peptide component, and used in practice of the present disclosure.

The nutritional composition(s) of the present disclosure including the peptide component, may be administered in one or more doses daily. Any orally acceptable dosage form is contemplated by the present disclosure. Examples of such dosage forms include, but are not limited to pills, tablets, capsules, soft-gels, liquids, liquid concentrates, powders, elixirs, solutions, suspensions, emulsions, lozenges, beads, cachets, and combinations thereof.

In some embodiments, the protein equivalent source comprising the peptide component may be added to a more complete nutritional product. In this embodiment, the nutritional composition may contain fat and carbohydrate sources or components and may be used to supplement the diet or may be used as the sole source of nutrition.

In some embodiments, the nutritional composition comprises at least one carbohydrate source. The carbohydrate source can be any used in the art, e.g., lactose, glucose, fructose, corn syrup solids, maltodextrins, sucrose, starch, rice syrup solids, and the like. The amount of the carbohydrate component in the nutritional composition typically can vary from between about 5 g/100 kcal and about 25 g/100 kcal. In some embodiments, the amount of carbohydrate is between about 6 g/100 kcal and about 22 g/100 kcal. In other embodiments, the amount of carbohydrate is between about 12 g/100 kcal and about 14 g/100 kcal. In some embodiments, corn syrup solids are preferred. Moreover, hydrolyzed, partially hydrolyzed, and/or extensively hydrolyzed carbohydrates may be desirable for inclusion in the nutritional composition due to their easy digestibility. Specifically, hydrolyzed carbohydrates are less likely to contain allergenic epitopes.

Non-limiting examples of carbohydrate materials suitable for use herein include hydrolyzed or intact, naturally or chemically modified, starches sourced from corn, tapioca, rice or potato, in waxy or non-waxy forms. Non-limiting examples of suitable carbohydrates include various hydrolyzed starches characterized as hydrolyzed cornstarch, maltodextrin, maltose, corn syrup, dextrose, corn syrup solids, glucose, and various other glucose polymers and combinations thereof. Non-limiting examples of other suitable carbohydrates include those often referred to as sucrose, lactose, fructose, high fructose corn syrup, indigestible oligosaccharides such as fructooligosaccharides and combinations thereof.

The nutritional composition may be protein-free in some embodiments and comprise free amino acids as an element of the protein equivalent source. In certain other embodiments, small amino acid peptides may be included as the protein component of the nutritional composition. Such small amino acid peptides may be naturally occurring or synthesized. The amount of free amino acids in the nutritional composition may vary from about 1 g/100 kcal to about 5 g/100 kcal.

The nutritional composition may also comprise a fat source. Suitable fat or lipid sources for the nutritional composition of the present disclosure may be any known or used in the art, including but not limited to, animal sources, e.g., milk fat, butter, butter fat, egg yolk lipid; marine sources, such as fish oils, marine oils, single cell oils; vegetable and plant oils, such as corn oil, canola oil, sunflower oil, soybean oil, palm olein oil, coconut oil, high oleic sunflower oil, evening primrose oil, rapeseed oil, olive oil, flaxseed (linseed) oil, cottonseed oil, high oleic safflower oil, palm stearin, palm kernel oil, wheat germ oil; medium chain triglyceride oils and emulsions and esters of fatty acids; and any combinations thereof.

In some embodiment the nutritional composition comprises between about 1.3 g/100 kcal to about 7.2 g/100 kcal of a fat source. In other embodiments the fat source may be present in an amount from about 2.5 g/100 kcal to about 6.0 g/100 kcal. In still other embodiments, the fat source may be present in the nutritional composition in an amount from about 3.0 g/100 kcal to about 4.0 g/100 kcal.

The nutritional composition may also contain one or more prebiotics (also referred to as a prebiotic source) in certain embodiments. Prebiotics can stimulate the growth and/or activity of ingested probiotic microorganisms, selectively reduce pathogens found in the gut, and favorably influence the short chain fatty acid profile of the gut. Such prebiotics may be naturally-occurring, synthetic, or developed through the genetic manipulation of organisms and/or plants, whether such new source is now known or developed later. Prebiotics useful in the present disclosure may include oligosaccharides, polysaccharides, and other prebiotics that contain fructose, xylose, soya, galactose, glucose and mannose.

More specifically, prebiotics useful in the present disclosure may include polydextrose, polydextrose powder, lactulose, lactosucrose, raffinose, gluco-oligosaccharide, inulin, fructo-oligosaccharide, isomalto-oligosaccharide, soybean oligosaccharides, lactosucrose, xylo-oligosaccharide, chito-oligosaccharide, manno-oligosaccharide, aribino-oligosaccharide, siallyl-oligosaccharide, fuco-oligosaccharide, galacto-oligosaccharide, and gentio-oligosaccharides. In some embodiments, the total amount of prebiotics present in the nutritional composition may be from about 0.1 g/100 kcal to about 1 g/100 kcal. In certain embodiments, the total amount of prebiotics present in the nutritional composition may be from about 0.3 g/100 kcal to about 0.7 g/100 kcal. Moreover, the nutritional composition may comprise a prebiotic component comprising polydextrose ("PDX") and/or galacto-oligosaccharide ("GOS"). In some embodiments, the prebiotic component comprises at least 20% GOS, PDX or a mixture thereof.

If PDX is used in the prebiotic composition, the amount of PDX in the nutritional composition may, in an embodiment, be within the range of from about 0.1 g/100 kcal to about 1 g/100 kcal. In another embodiment, the amount of polydextrose is within the range of from about 0.2 g/100 kcal to about 0.6 g/100 kcal. And in still other embodiments, the amount of PDX in the nutritional composition may be from about 0.1 mg/100 kcal to about 0.5 mg/100 kcal.

If GOS is used in the prebiotic composition, the amount of GOS in the nutritional composition may, in an embodiment, be from about 0.1 g/100 kcal to about 1 g/100 kcal. In another embodiment, the amount of GOS in the nutritional composition may be from about 0.2 g/100 kcal to about 0.5 g/100 kcal. In other embodiments, the amount of GOS in the nutritional composition may be from about 0.1 mg/100 kcal to about 1.0 mg/100 kcal or from about 0.1 mg/100 kcal to about 0.5 mg/100 kcal.

The nutritional composition of the present disclosure may also contain a source of long chain polyunsaturated fatty acids ("LCPUFAs"). Suitable LCPUFAs include, but are not limited to DHA, eicosapentaenoic acid ("EPA"), ARA, linoleic (18:2 n-6), γ-linolenic (18:3 n-6), dihomo-γ-linolenic (20:3 n-6) acids in the n-6 pathway, α-linolenic (18:3 n-3), stearidonic (18:4 n-3), eicosatetraenoic (20:4 n-3), eicosapentaenoic (20:5 n-3), and docosapentaenoic (22:6 n-3).

The amount of LCPUFA in the nutritional composition is at least about 5 mg/100 kcal, and may vary from about 5 mg/100 kcal to about 100 mg/100 kcal, more preferably from about 10 mg/100 kcal to about 50 mg/100 kcal.

Sources of LCPUFAs include dairy products like eggs and butterfat; marine oils, such as cod, menhaden, sardine, tuna and many other fish; certain animal fats, lard, tallow and microbial oils such as fungal and algal oils, or from any other resource fortified or not, form which LCPUFAs could be obtained and used in a nutritional composition. The LCPUFA could be part of a complex mixture obtained by separation technology known in the art aimed at enrichment of LCPUFAs and the derivatives or precursors of LCPUFAs in such mixtures.

The LCPUFAs may be provided in the nutritional composition in the form of esters of free fatty acids; mono-, di- and tri-glycerides; phosphoglyerides, including lecithins; and/or mixtures thereof. Additionally, LCPUFA may be provided in the nutritional composition in the form of phospholipids, especially phosphatidylcholine.

In an embodiment, especially if the nutritional composition is an infant formula, the nutritional composition is supplemented with both DHA and ARA. In this embodiment, the weight ratio of ARA:DHA may be between about 1:3 and about 9:1. In a particular embodiment, the weight ratio of ARA:DHA is from about 1:2 to about 4:1.

DHA is advantageously present in the nutritional composition, in some embodiments, from at least about 17 mg/100 kcal, and may vary from about 5 mg/100 kcal to about 75 mg/100 kcal. In some embodiments, DHA is present from about 10 mg/100 kcal to about 50 mg/100 kcal.

The nutritional composition may be supplemented with oils containing DHA and/or ARA using standard techniques known in the art. For example, DHA and ARA may be added to the composition by replacing an equivalent amount of an oil, such as high oleic sunflower oil, normally present in the composition. As another example, the oils containing DHA and ARA may be added to the composition by replacing an equivalent amount of the rest of the overall fat blend normally present in the composition without DHA and ARA.

If utilized, the source of DHA and/or ARA may be any source known in the art such as marine oil, fish oil, single cell oil, egg yolk lipid, and brain lipid. In some embodiments, the DHA and ARA are sourced from single cell Martek oils, DHASCO® and ARASCO®, or variations thereof. The DHA and ARA can be in natural form, provided that the remainder of the LCPUFA source does not result in any substantial deleterious effect on the infant. Alternatively, the DHA and ARA can be used in refined form.

In an embodiment, sources of DHA and ARA are single cell oils as taught in U.S. Pat. Nos. 5,374,567; 5,550,156; and 5,397,591, the disclosures of which are incorporated herein in their entirety by reference. However, the present disclosure is not limited to only such oils.

Furthermore, some embodiments of the nutritional composition may mimic certain characteristics of human breast milk. However, to fulfill the specific nutrient requirements of some subjects, the nutritional composition may comprise a higher amount of some nutritional components than does human milk. For example, the nutritional composition may comprise a greater amount of DHA than does human breast milk. The enhanced level of DHA of the nutritional composition may compensate for an existing nutritional DHA deficit.

In some embodiments, the nutritional composition may contain one or more probiotics. Any probiotic known in the art may be acceptable in this embodiment. In a particular embodiment, the probiotic may be selected from any *Lactobacillus* species, *Lactobacillus rhamnosus* GG (ATCC number 53103), *Bifidobacterium* species, *Bifidobacterium longum* BB536 (BL999, ATCC: BAA-999), *Bifidobacterium longum* AH1206 (NCIMB: 41382), *Bifidobacterium breve* AH1205 (NCIMB: 41387), *Bifidobacterium infantis* 35624 (NCIMB: 41003), and *Bifidobacterium animalis* subsp. *lactis* BB-12 (DSM No. 10140) or any combination thereof.

If included in the composition, the amount of the probiotic may vary from about $1\times10^4$ to about $1.5\times10^{10}$ cfu of probiotics per 100 kcal, more preferably from about $1\times10^6$ to about $1\times10^9$ cfu of probiotics per 100 kcal. In certain other embodiments the amount of probitic may vary from about $1\times10^7$ cfu/100 kcal to about $1\times10^8$ cfu/100 kcal.

In an embodiment, the probiotic(s) may be viable or non-viable. As used herein, the term "viable", refers to live microorganisms. The term "non-viable" or "non-viable probiotic" means non-living probiotic microorganisms, their cellular components and/or metabolites thereof. Such non-viable probiotics may have been heat-killed or otherwise inactivated, but they retain the ability to favorably influence the health of the host. The probiotics useful in the present disclosure may be naturally-occurring, synthetic or developed through the genetic manipulation of organisms, whether such source is now known or later developed.

Surprisingly, when the peptide component included in the protein equivalent source described herein was tested in conjunction with LGG+Lipil (ARA/DHA) supplementation, a reduction in weight gain in an experimental animal model of obesity was observed. Additionally, the administration of the peptide component in the protein equivalent source described herein, with LGG+Lipil (ARA/DHA) exhibited a beneficial effect on body mass composition. For example, there was a reduction in overall fat mass and lower cholesterol levels were observed.

Accordingly, in some embodiments, the nutritional compositions comprise the peptide component, LGG, and at least one long chain polyunsaturated fatty acid, selected from ARA or DHA. Without being bound by any particular theory, it is believed that a combination of these elements provides synergistic health benefits, such as promoting fat loss and lower cholesterol levels.

In some embodiments, rather than a probiotic itself, the nutritional composition(s) of the present disclosure may comprise a culture supernatant from a late-exponential growth phase of a probiotic batch-cultivation process (hereinafter referred to as the "culture supernatant"); in specific embodiments, the probiotic is LGG. Batch cultivation culture supernatant (which can also be referred to as "spent medium") may possesses protection against pathogen infection, including infection by *C. sakazakii*. Specifically the harvested culture supernatant may prevent the invasion of *C. sakazakii* to organs such as the brain and reduce mortality associated with *C. sakazakii*.

In some embodiments, the nutritional composition comprises a culture supernatant from a late-exponential growth phase of a probiotic batch-cultivation process, for use in the treatment or prevention of pathogen infection. In certain embodiments, the probiotic is LGG, and the pathogen is *C. sakazakii*.

Without wishing to be bound by theory, it is believed that the activity of the culture supernatant can be attributed to the mixture of components (including proteinaceous materials, and possibly including (exo)polysaccharide materials) as found released into the culture medium at a late stage of the exponential (or "log") phase of batch cultivation of LGG. The chemical composition of the culture supernatant is believed to be a mixture of a plurality of amino acids, oligo- and polypeptides, and proteins, of various molecular weights. The culture supernatant may further comprise polysaccharide structures and/or nucleotides. In some embodiments the culture supernatant pertains to the entire, i.e. unfractionated culture supernatant. Further, in some embodiments the culture supernatant pertains to the entire, i.e. unfractionated culture supernatant.

The stages recognized in batch cultivation of bacteria are known to the skilled person. These are the "lag," the "log" ("logarithmic" or "exponential"), the "stationary" and the "death" (or "logarithmic decline") phases. In all phases during which live bacteria are present, the bacteria metabolize nutrients from the media, and secrete (exert, release) materials into the culture medium. The composition of the secreted material at a given point in time of the growth stages is not generally predictable.

In some embodiments, a composition according to the disclosure and/or embodiments thereof is obtainable by a process comprising the steps of (a) subjecting a probiotic such as LGG to cultivation in a suitable culture medium using a batch process; (b) harvesting the culture supernatant at a late exponential growth phase of the cultivation step, which phase is defined with reference to the second half of the time between the lag phase and the stationary phase of the batch-cultivation process; (c) optionally removing low molecular weight constituents from the supernatant so as to retain molecular weight constituents above 5 kiloDaltons (kDa) or even above 6 kDa; (d) removing liquid contents from the culture supernatant so as to obtain the composition.

In the present disclosure and embodiments thereof, secreted materials are harvested from a late exponential phase. The late exponential phase occurs in time after the mid exponential phase (which is halftime of the duration of the exponential phase, hence the reference to the late exponential phase as being the second half of the time between the lag phase and the stationary phase). In particular, the term "late exponential phase" is used herein with reference to the latter quarter portion of the time between the lag phase and the stationary phase of the batch-cultivation process. In some embodiments of the present disclosure, harvesting of the culture supernatant is at a point in time of 75% to 85% of the duration of the exponential phase, and most preferably is at about ⅚ of the time elapsed in the exponential phase.

The term "cultivation" or "culturing" refers to the propagation of microorganisms, in this case LGG, on or in a suitable medium. Such a culture medium can be of a variety of kinds, and is particularly a liquid broth, as customary in the art. A preferred broth, e.g., is MRS broth as generally used for the cultivation of lactobacilli. MRS broth generally comprises polysorbate, acetate, magnesium and manganese, which are known to act as special growth factors for lactobacilli, as well as a rich nutrient base. A typical composition comprises (amounts in g/liter) peptone from casein 10.0; meat extract 8.0; yeast extract 4.0; D(+)-glucose 20.0; dipotassium hydrogen phosphate 2.0; Tween® 80 1.0; triammonium citrate 2.0; sodium acetate 5.0; magnesium sulphate 0.2; manganese sulphate 0.04.

In some embodiments, the culture supernatant of the present disclosure may be included in a nutritional composition that is an infant formula. The harvesting of secreted bacterial products brings about a problem that the culture media cannot easily be deprived of undesired components. This specifically relates to nutritional products for relatively vulnerable subjects, such as infant formula or clinical nutrition. This problem is not incurred if specific components from a culture supernatant are first isolated, purified, and then applied in a nutritional product. However, it is desired to make use of a more complete cultural supernatant. This would serve to provide a composition better reflecting the natural action of the probiotic (i.e. LGG). One cannot, however, just use the culture supernatant itself as a basis for non-viable probiotic materials to be specifically used in infant formula and the like.

In some embodiments, the culture supernatan harvested from LGG cultivation does not contain components (as may present in the culture medium) that are not desired, or generally accepted, in nutritional compositions, such as an infant formula. With reference to polysorbate regularly present in MRS broth, media for the culturing of bacteria may include an emulsifying non-ionic surfactant, e.g. on the basis of polyethoxylated sorbitan and oleic acid (typically available as Tween® polysorbates, such as Tween® 80). While these surfactants are frequently found in food products, e.g. ice cream, and are generally recognized as safe, they are not in all jurisdictions considered desirable, or even acceptable for use in nutritional products for relatively vulnerable subjects, such as infant formula or clinical nutrition.

The present disclosure thus, in some embodiments utilizes a culture media in which the aforementioned polysorbates can be avoided. To this end, a culture medium of the disclosure is devoid of polysorbates such as Tween 80. In a preferred embodiment of the disclosure and/or embodiments thereof the culture medium may comprise an oily ingredient selected from the group consisting of oleic acid, linseed oil, olive oil, rape seed oil, sunflower oil and mixtures thereof. It will be understood that the full benefit of the oily ingredient is attained if the presence of a polysorbate surfactant is essentially or entirely avoided.

The culture supernatant, in some embodiments, may have a neutral pH, such as a pH of between pH 5 and pH 7, preferably pH 6.

In addition to the foregoing, it should be noted that the batch cultivation of lactobacilli, including LGG, is common general knowledge available to the person skilled in the art. These methods thus do not require further elucidation here. The culture supernatant of the present disclosure can be harvested by any known technique for the separation of culture supernatant from a bacterial culture. Such techniques are well-known in the art and include, e.g., centrifugation, filtration, sedimentation, and the like.

The disclosed nutritional composition(s) may be provided in any form known in the art, such as a powder, a gel, a suspension, a paste, a solid, a liquid, a liquid concentrate, a reconstituteable powdered milk substitute or a ready-to-use product. The nutritional composition may, in certain embodiments, comprise a nutritional supplement, children's nutritional product, infant formula, human milk fortifier, growing-up milk or any other nutritional composition designed for an infant or a pediatric subject. Nutritional compositions of the present disclosure include, for example, orally-ingestible, health-promoting substances including, for example, foods, beverages, tablets, capsules and powders. Moreover, the nutritional composition of the present disclosure may be standardized to a specific caloric content, it may be provided as a ready-to-use product, or it may be provided in a concentrated form. In some embodiments, the nutritional composition is in powder form with a particle size in the range of 5 µm to 1500 µm, more preferably in the range of 10 µm to 300 µm.

If the nutritional composition is in the form of a ready-to-use product, the osmolality of the nutritional composition may be between about 100 and about 1100 mOsm/kg water, more typically about 200 to about 700 mOsm/kg water.

In certain embodiments, the nutritional composition is hypoallergenic. In other embodiments, the nutritional composition is kosher and/or halal. In still further embodiments, the nutritional composition contains non-genetically modified ingredients. In an embodiment, the nutritional formulation is sucrose-free. The nutritional composition may also be lactose-free. In other embodiments, the nutritional composition does not contain any medium-chain triglyceride oil. In some embodiments, no carrageenan is present in the composition. In other embodiments, the nutritional composition is free of all gums.

The nutritional composition of the present disclosure is not limited to compositions comprising nutrients specifically listed herein. Any nutrients may be delivered as part of the composition for the purpose of meeting nutritional needs and/or in order to optimize the nutritional status in a subject.

Moreover, in some embodiments, the nutritional composition is nutritionally complete, containing suitable types and amounts of lipids, carbohydrates, proteins, vitamins and minerals to be a subject's sole source of nutrition. Indeed, the nutritional composition may optionally include any number of proteins, peptides, amino acids, fatty acids, probiotics and/or their metabolic by-products, prebiotics, carbohydrates and any other nutrient or other compound that may provide many nutritional and physiological benefits to a subject. Further, the nutritional composition of the present disclosure may comprise flavors, flavor enhancers, sweeteners, pigments, vitamins, minerals, therapeutic ingredients, functional food ingredients, food ingredients, processing ingredients or combinations thereof.

The nutritional composition of the present disclosure may be standardized to a specific caloric content, it may be provided as a ready-to-use product, or it may be provided in a concentrated form.

In some embodiments, the nutritional composition of the present disclosure is a growing-up milk. Growing-up milks are fortified milk-based beverages intended for children over 1 year of age (typically from 1-3 years of age, from 4-6 years of age or from 1-6 years of age). They are not medical foods and are not intended as a meal replacement or a supplement to address a particular nutritional deficiency. Instead, growing-up milks are designed with the intent to serve as a complement to a diverse diet to provide additional insurance that a child achieves continual, daily intake of all essential vitamins and minerals, macronutrients plus additional functional dietary components, such as non-essential nutrients that have purported health-promoting properties.

The exact composition of a nutritional composition according to the present disclosure can vary from market-to-market, depending on local regulations and dietary intake information of the population of interest. In some embodiments, nutritional compositions according to the disclosure consist of a milk protein source, such as whole or skim milk, plus added sugar and sweeteners to achieve desired sensory properties, and added vitamins and minerals. The fat composition is typically derived from the milk raw materials. Total protein can be targeted to match that of human milk, cow milk or a lower value. Total carbohydrate is usually targeted to provide as little added sugar, such as sucrose or fructose, as possible to achieve an acceptable taste. Typically, Vitamin A, calcium and Vitamin D are added at levels to match the nutrient contribution of regional cow milk. Otherwise, in some embodiments, vitamins and minerals can be added at levels that provide approximately 20% of the dietary reference intake (DRI) or 20% of the Daily Value (DV) per serving. Moreover, nutrient values can vary between markets depending on the identified nutritional needs of the intended population, raw material contributions and regional regulations.

One or more vitamins and/or minerals may also be added in to the nutritional composition in amounts sufficient to supply the daily nutritional requirements of a subject. It is to be understood by one of ordinary skill in the art that vitamin and mineral requirements will vary, for example, based on the age of the child. For instance, an infant may have different vitamin and mineral requirements than a child between the ages of one and thirteen years. Thus, the embodiments are not intended to limit the nutritional composition to a particular age group but, rather, to provide a range of acceptable vitamin and mineral components.

In embodiments providing a nutritional composition for a child, the composition may optionally include, but is not limited to, one or more of the following vitamins or derivations thereof: vitamin $B_1$ (thiamin, thiamin pyrophosphate, TPP, thiamin triphosphate, TTP, thiamin hydrochloride, thiamin mononitrate), vitamin $B_2$ (riboflavin, flavin mononucleotide, FMN, flavin adenine dinucleotide, FAD, lactoflavin, ovoflavin), vitamin $B_3$ (niacin, nicotinic acid, nicotinamide, niacinamide, nicotinamide adenine dinucleotide, NAD, nicotinic acid mononucleotide, NicMN, pyridine-3-carboxylic acid), vitamin $B_3$-precursor tryptophan, vitamin $B_6$ (pyridoxine, pyridoxal, pyridoxamine, pyridoxine hydrochloride), pantothenic acid (pantothenate, panthenol), folate (folic acid, folacin, pteroylglutamic acid), vitamin $B_{12}$ (cobalamin, methylcobalamin, deoxyadenosylcobalamin, cyanocobalamin, hydroxycobalamin, adenosylcobalamin), biotin, vitamin C (ascorbic acid), vitamin A (retinol, retinyl acetate, retinyl palmitate, retinyl esters with other long-chain fatty acids, retinal, retinoic acid, retinol esters), vitamin D (calciferol, cholecalciferol, vitamin $D_3$, 1,25,-dihydroxyvitamin D), vitamin E ($\alpha$-tocopherol, $\alpha$-tocopherol acetate, $\alpha$-tocopherol succinate, $\alpha$-tocopherol nicotinate, $\alpha$-tocopherol), vitamin K (vitamin $K_1$, phylloquinone, naphthoquinone, vitamin $K_2$, menaquinone-7, vitamin $K_3$, menaquinone-4, menadione, menaquinone-8, menaquinone-8H, menaquinone-9, menaquinone-9H, menaquinone-10, menaquinone-11, menaquinone-12, menaquinone-13), choline, inositol, 6-carotene and any combinations thereof.

In embodiments providing a children's nutritional product, such as a growing-up milk, the composition may optionally include, but is not limited to, one or more of the following minerals or derivations thereof: boron, calcium, calcium acetate, calcium gluconate, calcium chloride, calcium lactate, calcium phosphate, calcium sulfate, chloride, chromium, chromium chloride, chromium picolonate, copper, copper sulfate, copper gluconate, cupric sulfate, fluoride, iron, carbonyl iron, ferric iron, ferrous fumarate, ferric orthophosphate, iron trituration, polysaccharide iron, iodide, iodine, magnesium, magnesium carbonate, magnesium hydroxide, magnesium oxide, magnesium stearate, magnesium sulfate, manganese, molybdenum, phosphorus, potassium, potassium phosphate, potassium iodide, potassium chloride, potassium acetate, selenium, sulfur, sodium, docusate sodium, sodium chloride, sodium selenate, sodium molybdate, zinc, zinc oxide, zinc sulfate and mixtures thereof. Non-limiting exemplary derivatives of mineral compounds include salts, alkaline salts, esters and chelates of any mineral compound.

The minerals can be added to growing-up milks or to other children's nutritional compositions in the form of salts such as calcium phosphate, calcium glycerol phosphate, sodium citrate, potassium chloride, potassium phosphate, magnesium phosphate, ferrous sulfate, zinc sulfate, cupric sulfate, manganese sulfate, and sodium selenite. Additional vitamins and minerals can be added as known within the art.

In an embodiment, the children's nutritional composition may contain between about 10 and about 50% of the maximum dietary recommendation for any given country, or between about 10 and about 50% of the average dietary recommendation for a group of countries, per serving, of vitamins A, C, and E, zinc, iron, iodine, selenium, and choline. In another embodiment, the children's nutritional composition may supply about 10-30% of the maximum dietary recommendation for any given country, or about 10-30% of the average dietary recommendation for a group of countries, per serving of B-vitamins. In yet another embodiment, the levels of vitamin D, calcium, magnesium, phosphorus, and potassium in the children's nutritional product may correspond with the average levels found in milk. In other embodiments, other nutrients in the children's nutritional composition may be present at about 20% of the maximum dietary recommendation for any given country, or about 20% of the average dietary recommendation for a group of countries, per serving.

The nutritional composition(s) of the present disclosure may optionally include one or more of the following flavoring agents, including, but not limited to, flavored extracts, volatile oils, cocoa or chocolate flavorings, peanut butter flavoring, cookie crumbs, vanilla or any commercially available flavoring. Examples of useful flavorings include, but are not limited to, pure anise extract, imitation banana extract, imitation cherry extract, chocolate extract, pure lemon extract, pure orange extract, pure peppermint extract, honey, imitation pineapple extract, imitation rum extract, imitation strawberry extract, grape and or grape seed extracts, apple extract, bilberry extract or vanilla extract; or volatile oils, such as balm oil, bay oil, bergamot oil, cedarwood oil, cherry oil, cinnamon oil, clove oil, or peppermint oil; peanut butter, chocolate flavoring, vanilla cookie crumb, butterscotch, toffee, and mixtures thereof. The amounts of flavoring agent can vary greatly depending upon the flavoring agent used. The type and amount of flavoring agent can be selected as is known in the art.

The nutritional compositions of the present disclosure may optionally include one or more emulsifiers that may be added for stability of the final product. Examples of suitable emulsifiers include, but are not limited to, lecithin (e.g., from egg or soy or any other plant and animal sources), alpha lactalbumin and/or mono- and di-glycerides, and mixtures thereof. Other emulsifiers are readily apparent to the skilled artisan and selection of suitable emulsifier(s) will depend, in part, upon the formulation and final product.

The nutritional compositions of the present disclosure may optionally include one or more preservatives that may also be added to extend product shelf life. Suitable preservatives include, but are not limited to, potassium sorbate, sodium sorbate, potassium benzoate, sodium benzoate, calcium disodium EDTA, and mixtures thereof.

The nutritional compositions of the present disclosure may optionally include one or more stabilizers. Suitable stabilizers for use in practicing the nutritional composition of the present disclosure include, but are not limited to, gum arabic, gum ghatti, gum karaya, gum tragacanth, agar, furcellaran, guar gum, gellan gum, locust bean gum, pectin, low methoxyl pectin, gelatin, microcrystalline cellulose, CMC (sodium carboxymethylcellulose), methylcellulose hydroxypropyl methyl cellulose, hydroxypropyl cellulose, DATEM (diacetyl tartaric acid esters of mono- and diglycerides), dextran, carrageenans, CITREM, and mixtures thereof.

The present disclosure further provides a method for promoting and/or maintaining a healthy body weight by providing a nutritional composition including a protein equivalent source comprising the peptide component disclosed herein. In some embodiments, 20% to 80% of the protein equivalent source comprises the peptide component and 20% to 80% of the protein equivalent source comprises intact protein, a partially hydrolyzed protein, or combinations thereof.

Further provided are methods for promoting a healthy body weight by stimulating adiponectin levels in a target subject. The method includes providing a nutritional composition comprising the protein equivalent source including the peptide component disclosed herein to the target subject.

Adiponectin is an adipocytokin mainly synthesized and secreted by adipose tissue. Structurally, adiponectin is a 247 amino-acid protein monomer which forms trimers which further polymerize into larger polymeric complexes varying in size between 180 kDa (hexameres; LMW) or 400-600 kDa (16-meres; HMW).

Adiponectin has several beneficial and protective effects. These effects include anti-inflammatory, vasculoprotective and anti-diabetic effects. Moreover, studies suggest that adiponectin may plan in important role in the pathophysiology of metabolic syndrome and coronary artery disease. (Huang, K. et al., "Plasma Adiponectin Levels and Blood Pressures in Nondiabetic Adolescent Females." The Journal of Clinical Endocrinology & Metabolism, 88(9): 4130-4134). In human studies, the plasma levels of adiponectin were consistently reported to correlate negatively with body mass index (BMI), waist circumference, plasma glucose, insulin, and triglycerides but positively with high-density-lipoprotein cholesterol (HDL).

Levels of adiponectin in human blood are between 5-20 μg/ml and are decreased in subjects with insulin resistance and type 2 diabetes, indeed adiponectin-deficient mice display diabetes. Moreover, adiponectin has been shown to promote insulin sensitivity in experimental models. Administration of adiponectin causes glucose-lowering effects and ameliorates insulin resistance. It is therefore beneficial to increase the level of adiponectin in human blood.

Accordingly, the present disclosure includes methods for increasing the plasma concentration of adiponectin in a target subject by administering the nutritional composition including a protein equivalent source comprising the peptide component described herein to a target subject. In some embodiments, the method includes increasing the plasma concentration of adiponectin in a target subject to between about 5-20 μg/ml by administering the nutritional composition of the present disclosure, which includes the peptide component described herein.

In some embodiments the target subject may be a pediatric subject. Further, in one embodiment, the nutritional composition provided to the pediatric subject may be an infant formula. The peptide component identified herein and added to the infant formula may be selected from a specific source and concentrations thereof may be adjusted to maximize health benefits. In another embodiment of this method, the nutritional composition comprising the peptide component disclosed herein is a growing up milk.

In embodiments when the nutritional composition is an infant formula, the composition may advantageously promote a healthy body, healthy body fat mass, stimulate adiponectin production, lower total cholesterol levels, or any combination thereof. More particularly, in some embodiments, an infant who consumes the aforementioned infant formula may, in some embodiments, experience these beneficial effects throughout childhood and into adulthood. Similarly, when the nutritional composition is a growing-up milk, a child who ingests the growing-up milk may experience these beneficial effects into adulthood, as well as during childhood.

Example 1

Example 1 describes the process by which subcutaneous adipose tissue was exposed to a certain casein hydrolysate fraction.

Subcutaneous adipose tissue was obtained from healthy lean or moderately overweight women undergoing plastic surgery. The procedure was approved by the ethical committee of the Heinrich-Heine-University (Düsseldorf, Germany). Preadipocytes were isolated by collagenase digestion. Isolated cell pellets were resuspended in DMEM/F12 medium supplemented with 10% FCS, seeded in six-well or 12-well culture dishes, respectively, and maintained at 37° C. with 5% $CO_2$. After reaching confluence (day 0 of differentiation), cell cultures were incubated incubated in an adipocyte differentiation medium (DMEM/F12, 33 mM biotin, 17 mmol/l d-panthothenic-acid, 66 nM insulin, 1 nM triiodo-L-thyronine, 100 nM cortisol, 10 mg/ml apo-transferrin, 50 mg/ml gentamycin, 0.25 mg/ml amphotericin B, 15 mM HEPES, 14 nM $NaHCO_3$, pH 7.4) with troglitazone (5 μM) for 3 days. Once differentiation was started the cells were further incubated in adipocyte differentiation medium with medium changes every 2-3 days for a total differentiation period of 14 days.

After the differentiation period (14 days), the adipocytes were challenged with extensive casein hydrolysate at different concentrations (0.01%, 0.1% and 1%, respectively) for 24 hours.

The isolated human preadipocytes were carefully counted and the same cell number per well was plated. After the differentiation period, the cells are treated with casein hydrolysate at 0.01%, 0.1% and 1%. After 24 hours, the supernatants were collected and stored at −20° C. for analysis of adipokine content with an ELISA kit.

The ELISA kits include a plate with wells that are coated with a primary antibody against human adiponectin. The supernatants are added and after the appropriate incubation time, the sample is washed so that only the adipokine bound to the antibody is left. Another buffer containing the secondary antibody conjugated with HRP is added to the wells. After the indicated incubation time, the excess of secondary antibody is removed by washing and the remaining HRP bound to the adipokine-antibody complex reacts when adding the TMB buffer. The reaction is stopped by adding an acidic solution and the reacting yellow colour is measured. The absorbance is proportional to the yellow colour which indicates the presence of the adipokine of interest. A standard curve is obtained by plotting the concentration of the standards versus their absorbances, interpolating from the standard curve the concentration of adipokine in the sample is calculated.

The kits included a standard of human recombinant adiponectin used to calculate the adiponectin concentration. Moreover, the kits include a Quality control high and low standards with known concentrations. The kit for adiponectin ELISA recognizes natural and recombinant human adiponectin (full length, mutation-modified trimer only forming and globular domain).

Once the incubation conditions were validated, and unspecific effects of the milk fractions alone were discarded, we assessed the adiponectin secretion in the supernatants of the adipocytes previously stimulated with casein hydrolysate.

The casein hydrolysate fraction ("APZ1") triggered a significant upregulation of adiponectin secretion at 1%. (290.6±56.6% vs. control, see FIG. 1), following a dose-dependent trend. The effect of the APZ1 fraction is independent of a single amino acid mixture (See. APAA6 representing a single amino acid mixture), the latter did not exert any significant effect on adiponectin secretion. (See. FIG. 1).

Formulation Examples

Table 3 provides an example embodiment of a peptide component including 5 peptides from Table 1 and 3 peptides selected from Table 2 that may comprise the peptide component described herein

TABLE 3

Nutrition profile of an example peptide component
Example of Selected Peptides
for Peptide Component

| |
| --- |
| SEQ ID NO 5 |
| SEQ ID NO 24 |
| SEQ ID NO 33 |
| SEQ ID NO 56 |
| SEQ ID NO 64 |
| SEQ ID NO 13 |
| SEQ ID NO 24 |
| SEQ ID NO 60 |

Table 4 provides an example embodiment of a peptide component including 5 peptides from Table 1, 3 peptides selected from Table 2, and an additional 10 peptides from Table 1 that may comprise the peptide component described herein.

TABLE 4

Nutrition profile of an example peptide component
Example of Selected Peptides
for Peptide Component

| |
| --- |
| SEQ ID NO 13 |
| SEQ ID NO 24 |
| SEQ ID NO 60 |
| SEQ ID NO 5 |
| SEQ ID NO 11 |
| SEQ ID NO 22 |
| SEQ ID NO 25 |
| SEQ ID NO 33 |
| SEQ ID NO 45 |
| SEQ ID NO 46 |
| SEQ ID NO 47 |
| SEQ ID NO 48 |
| SEQ ID NO 52 |
| SEQ ID NO 34 |
| SEQ ID NO 36 |
| SEQ ID NO 61 |
| SEQ ID NO 62 |
| SEQ ID NO 64 |

Table 5 provides an example embodiment of a nutritional composition according to the present disclosure and describes the amount of each ingredient to be included per 100 kcal serving.

TABLE 5

Nutrition profile of an example nutritional composition

| | per 100 kcal | |
| --- | --- | --- |
| Nutrient | Minimum | Maximum |
| Protein Equivalent Source (g) | 1.0 | 7.0 |
| Carbohydrates (g) | 6 | 22 |
| Fat (g) | 1.3 | 7.2 |
| Prebiotic (g) | 0.3 | 1.2 |
| DHA (g) | 4 | 22 |
| Beta glucan (mg) | 2.9 | 17 |
| Probiotics (cfu) | 0.5 | 5.0 |
| Vitamin A (IU) | $9.60 \times 10^5$ | $3.80 \times 10^8$ |
| Vitamin D (IU) | 134 | 921 |
| Vitamin E (IU) | 22 | 126 |
| Vitamin K (mcg) | 0.8 | 5.4 |
| Thiamin (mcg) | 2.9 | 18 |
| Riboflavin (mcg) | 63 | 328 |
| Vitamin B6 (mcg) | 68 | 420 |
| Vitamin B12 (mcg) | 52 | 397 |
| Niacin (mcg) | 0.2 | 0.9 |
| Folic acid (mcg) | 690 | 5881 |
| Panthothenic acid (mcg) | 8 | 66 |
| Biotin (mcg) | 232 | 1211 |
| Vitamin C (mg) | 1.4 | 5.5 |
| Choline (mg) | 4.9 | 24 |
| Calcium (mg) | 4.9 | 43 |
| Phosphorus (mg) | 68 | 297 |
| Magnesium (mg) | 54 | 210 |
| Sodium (mg) | 4.9 | 34 |
| Potassium (mg) | 24 | 88 |
| Chloride (mg) | 82 | 346 |
| Iodine (mcg) | 53 | 237 |
| Iron (mg) | 8.9 | 79 |
| Zinc (mg) | 0.7 | 2.8 |
| Manganese (mcg) | 0.7 | 2.4 |
| Copper (mcg) | 7.2 | 41 |

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

Although embodiments of the disclosure have been described using specific terms, devices, and methods, such description is for illustrative purposes only. The words used are words of description rather than of limitation. It is to be understood that changes and variations may be made by those of ordinary skill in the art without departing from the spirit or the scope of the present disclosure, which is set forth in the following claims. In addition, it should be understood that aspects of the various embodiments may be interchanged in whole or in part. For example, while methods for the production of a commercially sterile liquid nutritional supplement made according to those methods have been exemplified, other uses are contemplated. Therefore, the spirit and scope of the appended claims should not be limited to the description of the versions contained therein.

What is claimed is:
1. A nutritional composition comprising:
 (i) a carbohydrate;
 (ii) a fat; and
 (iii) a protein equivalent, wherein
  (a) at least 20% of the protein equivalent includes a casein hydrolysate having a molar mass distribution of greater than 500 Daltons, and

(b) at least 20% to 80% of the protein equivalent comprises a peptide component, wherein the peptide component consists of the following individual peptides: SEQ ID NO 4, SEQ ID NO 13, SEQ ID NO 17, SEQ ID NO 21, SEQ ID NO 24, SEQ ID NO 30, SEQ ID NO 31, SEQ ID NO 32, SEQ ID NO 51, SEQ ID NO 57, SEQ ID NO 60, and SEQ ID NO 63; further wherein the peptide component is present in amount of from about 0.2 g/100 kcals to about 5.6 g/100 kcals of the nutritional composition.

2. The nutritional composition of claim 1, wherein the peptide component further comprises at least 10 individual peptides selected from the group consisting of SEQ ID NO 1, SEQ ID NO 2, SEQ ID NO 3, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 14, SEQ ID NO 15, SEQ ID NO 16, SEQ ID NO 18, SEQ ID NO 19, SEQ ID NO 20, SEQ ID NO 22, SEQ ID NO 23, SEQ ID NO 25, SEQ ID NO 26, SEQ ID NO 27, SEQ ID NO 28, SEQ ID NO 29, SEQ ID NO 33, SEQ ID NO 34, SEQ ID NO 35, SEQ ID NO 36, SEQ ID NO 37, SEQ ID NO 38, SEQ ID NO 39, SEQ ID NO 40, SEQ ID NO 41, SEQ ID NO 42, SEQ ID NO 43, SEQ ID NO 44, SEQ ID NO 45, SEQ ID NO 46, SEQ ID NO 47, SEQ ID NO 48, SEQ ID NO 49, SEQ ID NO 50, SEQ ID NO 52, SEQ ID NO 53, SEQ ID NO 54, SEQ ID NO 55, SEQ ID NO 56, SEQ ID NO 58, SEQ ID NO 59, SEQ ID NO 61, SEQ ID NO 62, and SEQ ID NO 64.

3. The nutritional composition of claim 1, wherein the protein equivalent comprises partially hydrolyzed protein having a degree of hydrolysis of less than 40%.

4. The nutritional composition of claim 1, further comprising at least one long-chain polyunsaturated fatty acid.

5. The nutritional composition of claim 4, wherein the at least one long-chain polyunsaturated fatty acid is selected from the group consisting of docosahexaenoic acid and arachidonic acid.

6. The nutritional composition of claim 1, further comprising a culture supernatant from a late-exponential growth phase of a probiotic batch-cultivation process.

7. The nutritional composition of claim 1, further comprising a probiotic.

8. The nutritional composition of claim 1, further comprising a prebiotic.

9. A nutritional composition, comprising:
(i) a carbohydrate;
(ii) a fat; and
(iii) a protein equivalent; wherein
(a) at least 20% of the protein equivalent comprises a casein hydrolysate having a molar mass distribution of greater than 500 Daltons, and
(b) at least 20% of the protein equivalent comprises a peptide component, wherein the peptide component consists of at least 5 individual peptides selected from the group consisting of SEQ ID NO 1, SEQ ID NO 2, SEQ ID NO 3, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 14, SEQ ID NO 15, SEQ ID NO 16, SEQ ID NO 18, SEQ ID NO 19, SEQ ID NO 20, SEQ ID NO 22, SEQ ID NO 23, SEQ ID NO 25, SEQ ID NO 26, SEQ ID NO 27, SEQ ID NO 28, SEQ ID NO 29, SEQ ID NO 33, SEQ ID NO 34, SEQ ID NO 35, SEQ ID NO 36, SEQ ID NO 37, SEQ ID NO 38, SEQ ID NO 39, SEQ ID NO 40, SEQ ID NO 41, SEQ ID NO 42, SEQ ID NO 43, SEQ ID NO 44, SEQ ID NO 45, SEQ ID NO 46, SEQ ID NO 47, SEQ ID NO 48, SEQ ID NO 49, SEQ ID NO 50, SEQ ID NO 52, SEQ ID NO 53, SEQ ID NO 54, SEQ ID NO 55, SEQ ID NO 56, SEQ ID NO 58, SEQ ID NO 59, SEQ ID NO 61, SEQ ID NO 62, SEQ ID NO 64;

and at least 3 individual peptides selected from SEQ ID NO 4, SEQ ID NO 13, SEQ ID NO 17, SEQ ID NO 21, SEQ ID NO 24, SEQ ID NO 30, SEQ ID NO 31, SEQ ID NO 32, SEQ ID NO 51, SEQ ID NO 57, SEQ ID NO 60, SEQ ID NO 63, wherein the peptide component is present in the nutritional composition in an amount of from about 0.2 g/100 kcals to about 5.6 g/100 kcals.

10. The nutritional composition of claim 9, wherein the protein equivalent comprises partially hydrolyzed protein having a degree of hydrolysis of less than 40%.

11. The nutritional composition of claim 9, further comprising a prebiotic.

12. The nutritional composition of claim 9, further comprising a culture supernatant from a late-exponential growth phase of a probiotic batch-cultivation process.

13. The nutritional composition of claim 1, wherein the nutritional composition further comprises intact protein.

14. The nutritional composition of claim 9, wherein the nutritional composition further comprises intact protein.

15. The nutritional composition of claim 1, comprising from about 1 g to about 7 g of protein equivalent per 100 kcal of nutritional composition.

16. The nutritional composition of claim 9, comprising from about 1 g to about 7 g of protein equivalent per 100 kcal of nutritional composition.

17. The nutritional composition of claim 1, comprising from about 5 g/100 kcal to about 25 g/100 kcal of a carbohydrate.

18. The nutritional composition of claim 9, comprising from about 5 g/100 kcal to about 25 g/100 kcal of a carbohydrate.

* * * * *